US010660578B2

(12) United States Patent
Narasimhan et al.

(10) Patent No.: US 10,660,578 B2
(45) Date of Patent: May 26, 2020

(54) COMBINING ELECTRONIC MONITORING WITH INHALED PHARMACOLOGICAL THERAPY TO MANAGE CARDIAC ARRHYTHMIAS INCLUDING ATRIAL FIBRILLATION

(71) Applicant: InCarda Therapeutics, Inc., Newark, CA (US)

(72) Inventors: Rangachari Narasimhan, Saratoga, CA (US); Luiz Belardinelli, Palo Alto, CA (US); Carlos A. Schuler, Cupertino, CA (US)

(73) Assignee: InCarda Therapeutics, Inc., Newark, CA (US)

( * ) Notice: Subject to any disclaimer, the term of this patent is extended or adjusted under 35 U.S.C. 154(b) by 0 days.

(21) Appl. No.: 15/928,851

(22) Filed: Mar. 22, 2018

(65) Prior Publication Data
US 2018/0303435 A1    Oct. 25, 2018

Related U.S. Application Data

(63) Continuation of application No. 15/422,053, filed on Feb. 1, 2017, now Pat. No. 10,010,294.

(60) Provisional application No. 62/289,473, filed on Feb. 1, 2016.

(51) Int. Cl.
| *A61B 5/00* | (2006.01) |
| *A61K 9/00* | (2006.01) |
| *A61K 47/12* | (2006.01) |
| *A61K 9/08* | (2006.01) |
| *A61K 9/10* | (2006.01) |
| *A61M 11/00* | (2006.01) |
| *A61M 15/00* | (2006.01) |
| *A61K 9/19* | (2006.01) |
| *A61B 5/046* | (2006.01) |
| *A61B 5/0404* | (2006.01) |
| *A61B 5/042* | (2006.01) |
| *A61B 5/0432* | (2006.01) |
| *A61B 5/044* | (2006.01) |
| *A61B 5/0452* | (2006.01) |
| *A61K 31/4458* | (2006.01) |
| *A61M 11/06* | (2006.01) |

(52) U.S. Cl.
CPC .......... *A61B 5/7405* (2013.01); *A61B 5/0006* (2013.01); *A61B 5/0022* (2013.01); *A61B 5/0031* (2013.01); *A61B 5/042* (2013.01); *A61B 5/0404* (2013.01); *A61B 5/044* (2013.01); *A61B 5/046* (2013.01); *A61B 5/0432* (2013.01); *A61B 5/0452* (2013.01); *A61B 5/4839* (2013.01); *A61B 5/6898* (2013.01); *A61K 9/008* (2013.01); *A61K 9/0019* (2013.01); *A61K 9/0078* (2013.01); *A61K 9/08* (2013.01); *A61K 9/10* (2013.01); *A61K 9/19* (2013.01); *A61K 31/4458* (2013.01); *A61K 47/12* (2013.01); *A61M 11/00* (2013.01); *A61M 15/00* (2013.01); *A61M 15/009* (2013.01); *A61M 15/0085* (2013.01); *A61B 2562/222* (2013.01); *A61M 11/005* (2013.01); *A61M 11/06* (2013.01); *A61M 2205/18* (2013.01); *A61M 2205/3303* (2013.01); *A61M 2205/3523* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/52* (2013.01); *A61M 2230/04* (2013.01)

(58) Field of Classification Search
CPC .................................................. A61B 5/7405
USPC .......................................................... 514/331
See application file for complete search history.

(56) References Cited

U.S. PATENT DOCUMENTS

| 3,991,761 A | 11/1976 | Cocozza |
| 4,069,819 A | 1/1978 | Valentini et al. |
| 4,114,615 A | 9/1978 | Wetterlin |
| 4,247,066 A | 1/1981 | Frost et al. |
| 4,338,931 A | 7/1982 | Cavazza |
| 4,846,876 A | 7/1989 | Draber et al. |
| 4,962,095 A | 10/1990 | Grover et al. |
| 4,995,385 A | 2/1991 | Valentini et al. |
| 5,458,135 A | 10/1995 | Patton et al. |
| 5,619,985 A | 4/1997 | Ohki et al. |
| 5,785,049 A | 7/1998 | Smith et al. |
| 5,855,913 A | 1/1999 | Hanes et al. |
| 5,874,064 A | 2/1999 | Edwards et al. |
| 5,922,675 A | 7/1999 | Baker et al. |
| 5,976,574 A | 11/1999 | Gordon |
| 5,985,248 A | 11/1999 | Gordon et al. |
| 5,985,309 A | 11/1999 | Edwards et al. |
| 6,001,336 A | 12/1999 | Gordon |
| 6,051,256 A | 4/2000 | Platz et al. |

(Continued)

FOREIGN PATENT DOCUMENTS

| AU | 2013248242 A1 | 11/2013 |
| EP | 1276474 B1 | 6/2007 |

(Continued)

OTHER PUBLICATIONS

International Search Report and Written Opinion dated Apr. 18, 2017 for International PCT Patent Application No. PCT/US2017/016018.

(Continued)

*Primary Examiner* — Taofiq A Solola
(74) *Attorney, Agent, or Firm* — Wilson Sonsini Goodrich & Rosati

(57) ABSTRACT

Disclosed herein are methods of treating cardiac arrhythmia with electronic monitoring in a timely manner. Also disclosed herein are systems for electronic monitoring of cardiac arrhythmia.

18 Claims, 11 Drawing Sheets

(56) References Cited

U.S. PATENT DOCUMENTS

| | | | |
|---|---|---|---|
| 6,077,543 | A | 6/2000 | Gordon et al. |
| 6,257,233 | B1 | 7/2001 | Burr et al. |
| 6,357,490 | B1 | 3/2002 | Johnston et al. |
| 6,358,530 | B1 | 3/2002 | Eljamal et al. |
| 6,372,258 | B1 | 4/2002 | Platz et al. |
| 6,503,480 | B1 | 1/2003 | Edwards et al. |
| 6,546,929 | B2 | 4/2003 | Burr et al. |
| 7,302,295 | B2 | 11/2007 | Stahmann et al. |
| 7,473,433 | B2 | 1/2009 | Weickert et al. |
| 8,641,631 | B2 | 2/2014 | Sierra et al. |
| 8,974,828 | B2 | 3/2015 | Schuler et al. |
| 10,010,294 | B2 | 7/2018 | Narasimhan et al. |
| 1,004,593 | A1 | 8/2018 | Schuler et al. |
| 2002/0017295 | A1 | 2/2002 | Weers et al. |
| 2002/0115655 | A1 | 8/2002 | Mehanna et al. |
| 2003/0005924 | A1 | 1/2003 | Rabinowitz et al. |
| 2003/0079742 | A1 | 5/2003 | Giroux |
| 2003/0144701 | A1 | 7/2003 | Mehra et al. |
| 2004/0011358 | A1 | 1/2004 | Smaldone et al. |
| 2004/0035413 | A1 | 2/2004 | Smaldone et al. |
| 2004/0045546 | A1 | 3/2004 | Hirsh et al. |
| 2004/0099269 | A1 | 5/2004 | Hale et al. |
| 2004/0105820 | A1 | 6/2004 | Weers et al. |
| 2004/0156792 | A1 | 8/2004 | Tarara et al. |
| 2004/0167228 | A1 | 8/2004 | Rabinowitz et al. |
| 2005/0009776 | A1 | 1/2005 | Gadgil et al. |
| 2005/0070552 | A1 | 3/2005 | Fedida et al. |
| 2005/0211245 | A1 | 9/2005 | Smaldone et al. |
| 2005/0211253 | A1 | 9/2005 | Smaldone et al. |
| 2005/0235987 | A1 | 10/2005 | Smaldone et al. |
| 2006/0034847 | A1 | 2/2006 | Yun et al. |
| 2006/0034906 | A1 | 2/2006 | Boni et al. |
| 2006/0052333 | A1 | 3/2006 | Belardinelli et al. |
| 2006/0120962 | A1 | 6/2006 | Rabinowitz et al. |
| 2007/0122352 | A1 | 5/2007 | Kunka et al. |
| 2007/0122353 | A1 | 5/2007 | Hale et al. |
| 2007/0282177 | A1 | 12/2007 | Pilz |
| 2008/0038363 | A1 | 2/2008 | Zaffaroni et al. |
| 2008/0226736 | A1 | 9/2008 | Caponetti et al. |
| 2008/0269625 | A1 | 10/2008 | Halperin et al. |
| 2008/0275036 | A1 | 11/2008 | Cross et al. |
| 2010/0086606 | A1 | 4/2010 | Ogawa et al. |
| 2012/0003318 | A1 | 1/2012 | Schuler et al. |
| 2014/0290647 | A1 | 10/2014 | Salvinelli et al. |
| 2015/0313842 | A1 | 11/2015 | Schuler et al. |
| 2018/0296480 | A1 | 10/2018 | Schuler et al. |
| 2018/0318213 | A1 | 11/2018 | Schuler et al. |
| 2018/0325818 | A1 | 11/2018 | Schuler |

FOREIGN PATENT DOCUMENTS

| | | |
|---|---|---|
| JP | 2002529393 A | 9/2002 |
| RU | 38570 U1 | 7/2004 |
| WO | WO-9003144 A1 | 4/1990 |
| WO | WO-9524183 A1 | 9/1995 |
| WO | WO-9531479 A1 | 11/1995 |
| WO | WO-9632096 A1 | 10/1996 |
| WO | WO-9632149 A1 | 10/1996 |
| WO | WO-9916419 A1 | 4/1999 |
| WO | WO-9916420 A1 | 4/1999 |
| WO | WO-9916421 A1 | 4/1999 |
| WO | WO-9916422 A1 | 4/1999 |
| WO | WO-0007572 A2 | 2/2000 |
| WO | WO-0027359 A1 | 5/2000 |
| WO | WO-0072904 A1 | 12/2000 |
| WO | WO-0185136 A2 | 11/2001 |
| WO | WO-0185137 A2 | 11/2001 |
| WO | WO-0228377 A1 | 4/2002 |
| WO | WO-02083220 A2 | 10/2002 |
| WO | WO-02094236 A1 | 11/2002 |
| WO | WO-2004071368 A2 | 8/2004 |
| WO | WO-2005079897 A1 | 9/2005 |
| WO | WO-2007042467 A1 | 4/2007 |
| WO | WO-2007050347 A1 | 5/2007 |
| WO | WO-2008036247 A1 | 3/2008 |
| WO | WO-2008051621 A2 | 5/2008 |
| WO | WO-2008066745 A1 | 6/2008 |
| WO | WO-2008072190 A2 | 6/2008 |
| WO | WO-2008134630 A1 | 11/2008 |
| WO | WO-2010019914 A2 | 2/2010 |
| WO | WO-2010022259 A1 | 2/2010 |
| WO | WO-2010042658 A1 | 4/2010 |
| WO | WO-2010107964 A1 | 9/2010 |
| WO | WO-2012024106 A2 | 2/2012 |
| WO | WO-2014191837 A2 | 12/2014 |
| WO | WO-2015079197 A1 | 6/2015 |
| WO | WO-2017136421 A1 | 8/2017 |

OTHER PUBLICATIONS

Office Action dated Jul. 24, 2017 for U.S. Appl. No. 15/422,053.
U.S. Appl. No. 15/422,053 Notice of Allowance dated Mar. 5, 2018.
Abarbanell, et al. Prehospital management of rapid atrial fibrillation: recommendations for treatment protocols. Am J Emerg Med. Jan. 2001;19(1):6-9.
Barbato, et al. Role of beta2 adrenergic receptors in human atherosclerotic coronary arteries. Circulation. 2005, 111:288-294.
Borlak, et al. Metabolism of verapamil in cultures of rat alveolar epithelial cells and pharmacokinetics after administration by intravenous and inhalation routes. Drug Metab Dispos. Aug. 2005;33(8):1108-14. Epub May 10, 2005.
Co-pending U.S. Appl. No. 16/172,456, filed Oct. 26, 2018.
Dell'Orfano, et al. Drugs for Conversion of Atrial Fibrillation. Am. Fam. Physician. 58(2); 471-480, Aug. 1, 1998. 6 pages.
Deneer, et al. Absorption kinetics and pharmacodynamics of two oral dosage forms of flecainide in patients with an episode of paroxysmal atrial fibrillation. Eur J Clin Pharmacol. Dec. 2004;60(10):693-701.
European Office Action dated Nov. 16, 2017 for European Patent Application No. EP10754091.6.
European search report and search opinion dated Jan. 21, 2014 for EP Application No. 10754091.6.
Feldman, et al. Analysis of Coronary Response to Various Doses of Intracoronary Nitroglycerin. Circulation. 1982, 66:321-327.
Gaglione, et al. Is There Coronary Vasoconstriction after Intracoronary Beta-adrenergic Blockade in Patients with Coronary Artery Disease. J Am Coll Cardiol. 1987, 10:299-310.
Harrison, et al. Effect of Single Doses of Inhaled Lignocaine on FEV1 and Bronchial Reactivity in Asthma. Respir Med. Dec. 1992, 12:1359-635.
International search report and written opinion dated Jul. 12, 2010 for PCT Application No. PCT/US2010/027740.
Lopez-Vidriero, M.T. Issues relating to safety and efficacy in nebulizer use. Eur. Respir. Rev., 2000, 10:72, 210-212.
Noguchi, et al. Effects of Intracoronary Propranolol on Coronary Blood Flow and Regional Myocardial Function in Dogs. Eur J Pharmacol. 1987, 144(2):201-10.
Notice of allowance dated Jan. 21, 2015 for U.S. Appl. No. 13/257,249.
Office action dated Jan. 3, 2013 for U.S. Appl. No. 13/257,249.
Office Action dated Apr. 17, 2017 for U.S. Appl. No. 14/632,252.
Office Action dated Apr. 27, 2016 for U.S. Appl. No. 14/632,252.
Office action dated Jun. 20, 2014 for U.S. Appl. No. 13/257,249.
Office action dated Sep. 9, 2015 for U.S. Appl. No. 14/632,252.
Office action dated Sep. 26, 2013 for U.S. Appl. No. 13/257,249.
Office Action dated Dec. 1, 2016 for U.S. Appl. No. 14/632,252.
PCT/US2018/032092 International Search Report and Written Opinion dated Aug. 1, 2018.
Rabinowitz, et al. Ultra-fast absorption of amorphous pure drug aerosols via deep lung inhalation. J Pharm Sci. Nov. 2006;95(11):2438-51.
Razavi, M. Safe and effective pharmacologic management of arrhythmias. Tex Heart Inst J. 2005;32(2):209-11.
Suttorp, et al. The value of class IC antiarrhythmic drugs for acute conversion of paroxysmal atrial fibrillation or flutter to sinus rhythm. J Am Coll Cardiol. Dec. 1990;16(7):1722-7.
Twiss, et al. Efficacy of Calcium Channel Blockers as Maintenance Therapy for Asthma. British J of Clinical Pharmacology. Nov. 2001.

(56) References Cited

OTHER PUBLICATIONS

U.S. Appl. No. 14/632,252 Notice of Allowance dated Mar. 29, 2018.
U.S. Appl. No. 16/013,165 Office Acton dated Aug. 28, 2018.
U.S. Appl. No. 16/013,178 Office Action dated Sep. 18, 2018.
Zalewski, et al. Myocardial Protection during Transient Coronary Artery Occlusion in Man: Beneficial Effects of Regional Beta-adrenergic Blockade. Circulation. 1986, 73:734-73.
European Search Report dated Sep. 2, 2019 for EP Application No. 19176305.1.
European Search Report dated Sep. 4, 2019 for EP Application No. 19176272.3.
Ikeda, "Effects of Flecainide on the Electrophysiologic Properties of Isolated Canine and Rabbit Myocardial Fibers", JACC, vol. 5, No. 2, pp. 303-310, Feb. 1985.
Juan Tamargo et al., "Narrow therapeutic index drugs: a clinical pharmacological consideration to flecainide", Eur J Clin Pharmacol, vol. 71, 549-567, 2015.
Kroemer, "Flecainide enantiomers: Disposition i human subjects and electrophysiologic actions in vitro", Clinical Pharmacology & Therapeutics, vol. 46, Issue 5, pp. 584-590, Nov. 1989.
Office Action dated Dec. 28, 2018 for U.S. Appl. No. 16/172,456.
Supplementary European Search Report dated Aug. 6, 2019 for EP Application No. 17748062.1.
U.S. Appl. No. 15/976,516 Office Action dated Mar. 19, 2019.
U.S. Appl. No. 16/013,178 Final Office Action dated May 10, 2019.
U.S. Appl. No. 16/013,165 Final Office Action dated May 9, 2019.
U.S. Appl. No. 16/172,456 Final Office Action dated Sep. 27, 2019.
Search Report dated Nov. 22, 2019 for Application No. 11201805788W, (2 pages).
Written Opinion dated Nov. 29, 2019 for Application No. 11201805788W, (6 pages).

COMBINING ELECTRONIC MONITORING WITH INHALED PHARMACOLOGICAL THERAPY TO MANAGE CARDIAC ARRHYTHMIAS INCLUDING ATRIAL FIBRILLATION

CROSS-REFERENCE

This application is a continuation of U.S. application Ser. No. 15/422,053 filed on Feb. 1, 2017, which claims priority to U.S. provisional application No. 62/289,473, filed on Feb. 1, 2016; each of which is incorporated by reference in its entirety.

BACKGROUND

The disclosure relates to the use of inhaled CV therapies in combination with electronic monitoring devices.

Cardiac arrhythmia (also dysrhythmia) is a term for any of a large and heterogeneous group of conditions in which there can be abnormal electrical activity in the heart. The heart beat may be too fast or too slow, and may be regular or irregular.

Cardiac Arrhythmia is a field with a high level of unmet clinical need. Many drugs used today have been on the market since the early 1980s and 1990s and are mostly inadequate due to either lack of efficacy or a side-effect profile that can be primarily cardiac related, that necessitates extensive monitoring of the subject.

Atrial Fibrillation is a type of Cardiac arrhythmia that occurs as both symptomatic and asymptomatic. When symptomatic the subject goes to the ER in the hospital for treatment while when asymptomatic that subject does not realize that they are in an arrhythmic state. Atrial fibrillation normally occurs asymptomatically before it becomes symptomatic in short durations. These short episodes spontaneously convert into normal sinus rhythm. But the cumulative effect of these short episodes add to the overall AF burden and eventual progression of the disease.

Paroxysmal atrial fibrillation (PAF) is a subset of the overall Atrial Fibrillation (AF) population and is estimated to be a third of the overall AF population. AF affects about 34 million people worldwide and 11.3 million of these people worldwide are diagnosed as subjects with PAF.

Arrhythmias frequently result in emergency room (ER) visits, where intravenous drugs are administered, and sometimes necessitating extended stay in hospital and in some cases also leading to unplanned invasive procedures.

Ablation can be expensive and can be about 50% efficacious. Despite the high expense, ablation may not completely correct the arrhythmia. Often, multiple ablation procedures are required to achieve a satisfactory result in a subject's lifetime. Ablation also results in heart related medical complications associated with morbidity and mortality.

Electronic Monitoring systems are used in subjects to monitor if they are experiencing such arrhythmias and when an arrhythmia is sustained they are recorded and the treating physician is able to assess the course of therapy.

What is needed for slowing the progression of AF from its starting paroxysmal state to permanent AF.

None of the current oral or IV approved drug products are combined with an electronic monitoring system with the goal to terminate the arrhythmia at initiation thereby reducing the progression of the disease, the overall AF burden leading to significant reduction in the economies of hospital costs.

Exemplary monitoring devices include the AliveCor Mobile ECG, the Reveal LINQ Insertable Cardiac Monitor, the iRhythm ZIO XT Patch, the HeartCheck pen, the AfibAlert, smartphone or portable music player applications designed to detect arrhythmias, the Microlife AFIB Technology device, the WatchBP device, Holter monitors, Smart watches, wearable technology such as those that can vibrate as a means to detect an arrhythmia, or any other similar devices.

SUMMARY

Disclosed herein are methods of treating cardiac arrhythmia in a subject, comprising: (a) identifying cardiac arrhythmia in the subject with the aid of an electronic monitoring device; (b) aerosolizing a pharmaceutical composition in less than about 9 minutes using an inhaler, wherein the pharmaceutical composition can comprise of a therapeutically effective amount of at least one antiarrhythmic or a pharmaceutically acceptable salt thereof; and (c) administering the aerosolized pharmaceutical composition to the subject; thereby treating the cardiac arrhythmia. In some embodiments, the identifying of (a) includes an establishing of a duration of the cardiac arrhythmia. In some embodiments, the duration of the cardiac arrhythmia can be at least about 2 hours. In some embodiments, the duration of the cardiac arrhythmia can be at least about 1 hour. In some embodiments, the duration of the cardiac arrhythmia can be at least about 0.5 hours. In some embodiments, the aerosolizing of the pharmaceutical composition occurs in less than 6 minutes. In some embodiments, the aerosolizing of the pharmaceutical composition occurs in less than 3 minutes. In some embodiments, the therapeutically effective amount can be an amount sufficient to convert the arrhythmia to normal sinus rhythm. In some embodiments, the therapeutically effective amount can be at least about 60 mg of the at least one antiarrhythmic or a pharmaceutically acceptable salt thereof. In some embodiments, the therapeutically effective amount can be at least about 50 mg of the at least one antiarrhythmic or a pharmaceutically acceptable salt thereof. In some embodiments, the therapeutically effective amount can be at least about 40 mg of the at least one antiarrhythmic or a pharmaceutically acceptable salt thereof. In some embodiments, the therapeutically effective amount can be at least about 30 mg of the at least one antiarrhythmic or a pharmaceutically acceptable salt thereof. In some embodiments, the therapeutically effective amount converts the arrhythmia to normal sinus rhythm from about 0 secs to about 2 hours after the administration. In some embodiments, the therapeutically effective amount converts the arrhythmia to normal sinus rhythm in about 60 mins after administration. In some embodiments, the treating occurs within about 120 minutes from an onset of the cardiac arrhythmia. In some embodiments, the treating occurs within about 90 minutes from an onset of the cardiac arrhythmia. In some embodiments, the treating occurs within about 60 minutes from an onset of the cardiac arrhythmia. In some embodiments, the administering can comprise inhalation. In some embodiments, prior to (a), an electronic monitoring chip can be inserted into the subject. In some embodiments, an electronic monitoring chip can be worn by the subject. In some embodiments, the electronic monitoring chip can be in communication with the electronic monitoring device. In some embodiments, the communication can be a wireless communication. In some embodiments, prior to (a), an electronic monitoring chip can be inserted into the electronic monitoring device. In some embodiments, the identifying of (a) can comprise a communication of a result to the subject. In some embodiments, the communication can comprise an instruction to administer the pharmaceutical composition. In some embodiments, the instruction to administer can comprise a dosage of the aerosolized pharmaceutical composition to administer. In some embodiments, the administering can be performed by the subject. In some embodiments, the administering can be performed by a healthcare professional. In some embodiments, the healthcare professional can override a recommendation made by the electronic monitoring device. In some embodiments, the electronic monitoring device waits for a confirmation from the healthcare provider prior to allowing the administering of the aerosolized pharmaceutical composition to the subject. In some embodiments, the communication can comprise making a treatment recommendation. In some embodiments, the treatment recommendation can comprise restricting the administration of the pharmaceutical composition when the electronic monitoring device does not identify an arrhythmia. In some embodiments, the identifying of (a) can comprise a communication of a result to a healthcare professional. In some embodiments, the administering can be performed by the subject. In some embodiments, the administering can be performed by a healthcare professional. In some embodiments, the healthcare professional can be a paramedic. In some embodiments, the healthcare professional can be a physician. In some embodiments, the healthcare professional can be a monitoring professional. In some embodiments, the healthcare professional can override a recommendation made by the electronic monitoring device. In some embodiments, the electronic monitoring device waits for a confirmation from the healthcare provider prior to allowing the administering of the aerosolized pharmaceutical composition to the subject. In some embodiments, the communication can comprise making a treatment recommendation. In some embodiments, the treatment recommendation can comprise restricting the administration of the pharmaceutical composition when the electronic monitoring device does not identify an arrhythmia. In some embodiments, the at least one antiarrhythmic or salt thereof can be a class I antiarrhythmic. In some embodiments, the class I antiarrhythmic can be a class Ia, Ib, or Ic antiarrhythmic. In some embodiments, the class I antiarrhythmic can be flecainide or a salt thereof. In some embodiments, the at least one antiarrhythmic or salt thereof can be a class II antiarrhythmic. In some embodiments, the at least one antiarrhythmic or salt thereof can be a class III antiarrhythmic. In some embodiments, the at least one antiarrhythmic or salt thereof can be a class IV antiarrhythmic. In some embodiments, the at least one antiarrhythmic or salt thereof can be a class V antiarrhythmic. In some embodiments, the at least one antiarrhythmic or salt thereof can comprise a sodium channel blocker. In some embodiments, the at least one antiarrhythmic or salt thereof can comprise a potassium channel blocker. In some embodiments, the at least one antiarrhythmic or salt thereof can comprise a calcium channel blocker. In some embodiments, the at least one antiarrhythmic or salt thereof can be rapidly absorbed through a subject's lungs. In some embodiments, the at least one antiarrhythmic or salt thereof can be delivered to a subject's heart after being absorbed through the subject's lungs. In some embodiments, the inhaler can be in communication with the electronic monitoring device. In some embodiments, the communication can be a wired communication. In some embodiments, the communication can be a wireless communication. In some embodiments, the administering of the aerosolized pharmacological composition by the inhaler can be communicated to the electronic monitoring device. In some embodiments, the electronic monitoring device verifies the administering of the aerosolized pharmaceutical composition. In some embodiments, the electronic monitoring device continues monitoring the progress of the arrhythmia after the administration. In some embodiments, a recommendation to stop the administering can be communicated by the electronic monitoring device when the arrhythmia can be converted to a normal sinus rhythm. In some embodiments, a recommendation to seek medical attention can be communicated by the electronic monitoring device when the arrhythmia can be not responding to the administration of the pharmaceutical composition as determined by a continued incidence of arrhythmia at least about 2 hours after the administering. In some embodiments, the electronic monitoring device can comprise a digital display. In some embodiments, the electronic monitoring device can comprise auditory means capable of communicating to the subject. In some embodiments, the electronic monitoring device can be a smartphone. In some embodiments, the inhaler can comprise a digital display. In some embodiments, the inhaler can comprise auditory means capable of communicating to the subject.

Also disclosed herein are systems comprising: (a) an electronic monitoring chip; wherein the electronic monitoring chip monitors incidence of arrhythmia in a subject; (b) an electronic monitoring device; wherein the electronic monitoring device can be in wireless communication with the electronic monitoring chip; and (c) an inhaler; wherein the electronic monitoring device can be in communication with the inhaler. In some embodiments, the electronic monitoring device can be in communication with the inhaler through a wired connection. In some embodiments, the electronic monitoring device can be in communication with the inhaler through a wireless connection. In some embodiments, the electronic monitoring device can comprise a digital display. In some embodiments, the electronic monitoring device can comprise auditory means capable of communicating to the subject. In some embodiments, the electronic monitoring device can be a smartphone. In some embodiments, the electronic monitoring chip can be inserted into the subject. In some embodiments, the electronic monitoring chip can be worn by the subject. In some embodiments, the inhaler can comprise a digital display. In some embodiments, the inhaler can comprise auditory means capable of communicating to the subject. In some embodiments, the electronic monitoring device can comprise storage means. In some embodiments, subject data can be stored using the storage means. In some embodiments, the storage means can be a hard drive. In some embodiments, the storage means can be a cloud based storage.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features are set forth with particularity in the appended claims. A better understanding of features and advantages will be obtained by reference to the following detailed description that sets forth illustrative embodiments, in which exemplary principles are utilized, and the accompanying drawings of which:

DETAILED DESCRIPTION

Figure 1:
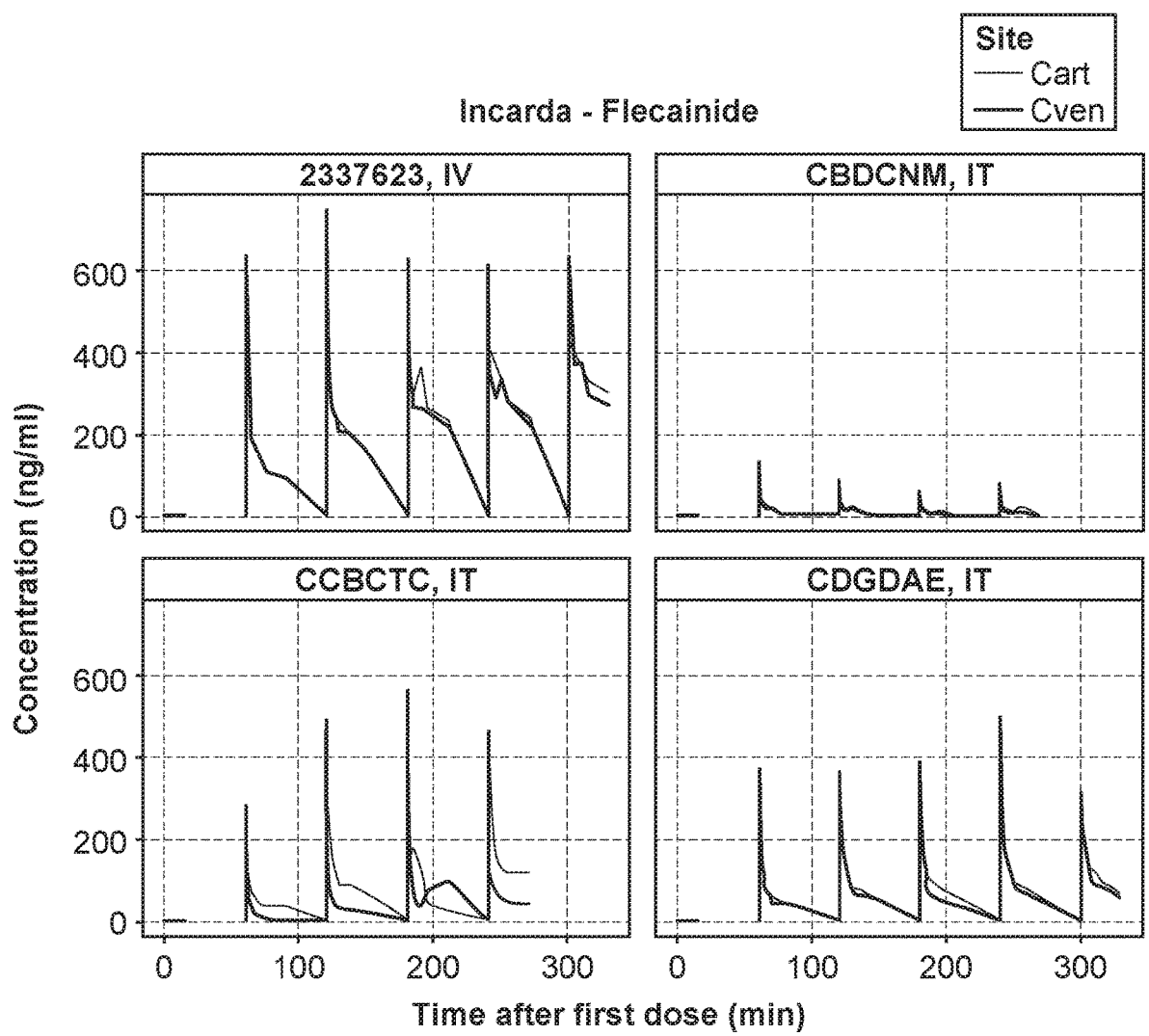
FIG. 1 depicts plots of the arterial and venous concentration of flecainide after intravenous or intra-tracheal administration.
Figure 2:
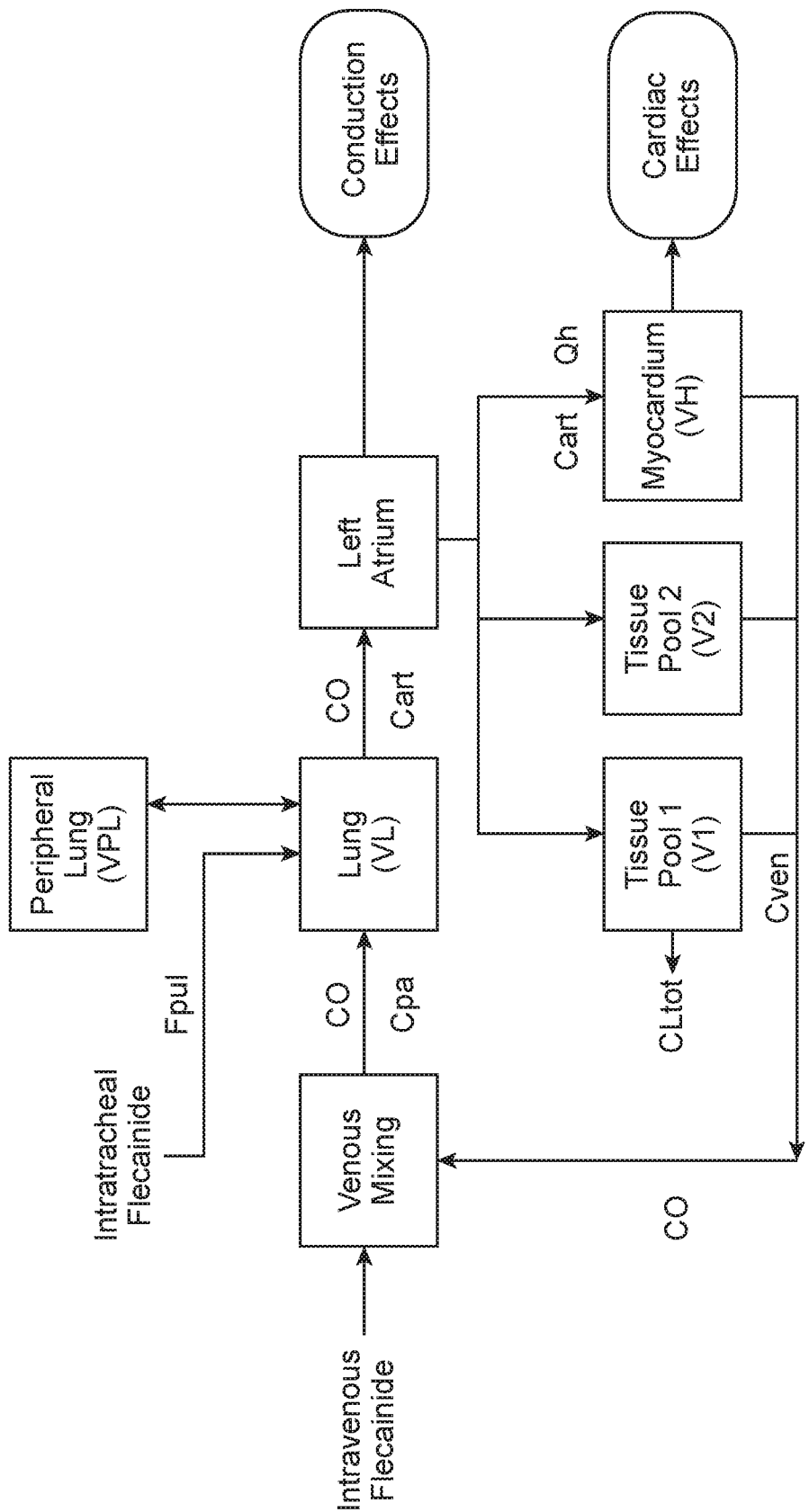
FIG. 2 depicts an exemplary physiologically based pharmacokinetic (PBPK) model of the intravenous or intra-tracheal administration of flecainide.
Figure 3:
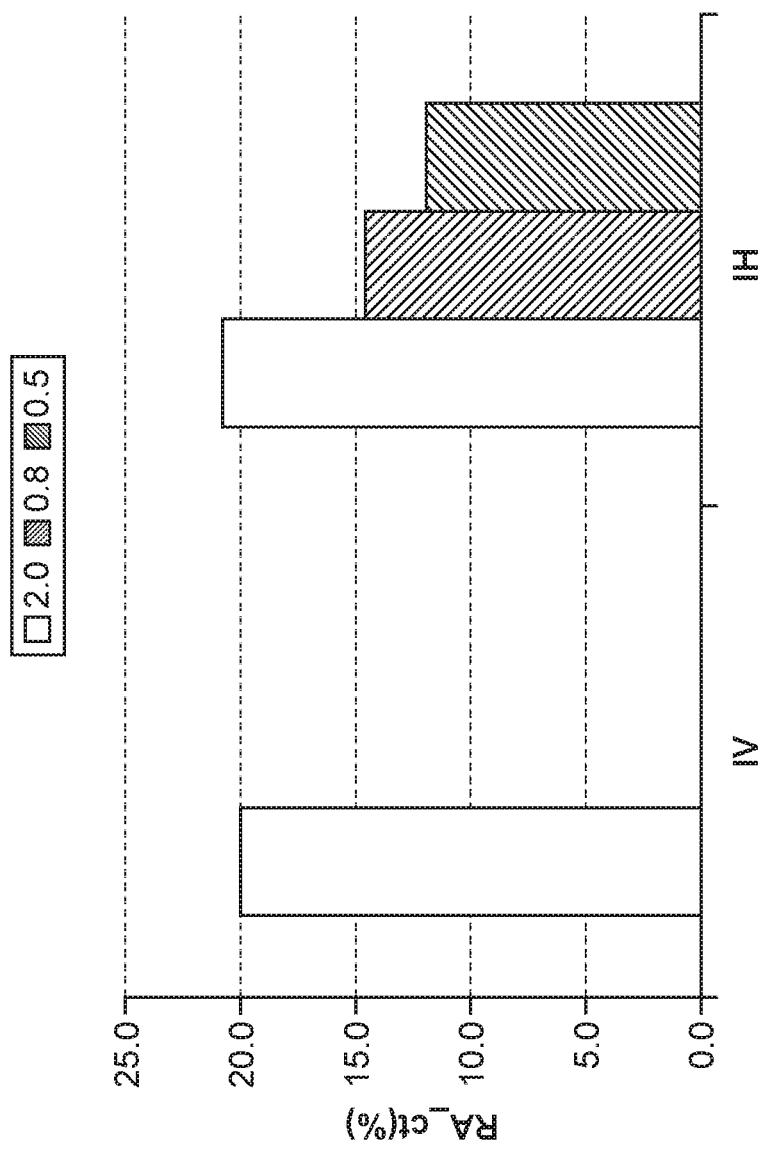
FIG. 3 depicts a plot of the effect on left atrial conduction time after administration via intravenous injection or inhalation.
Figure 4:
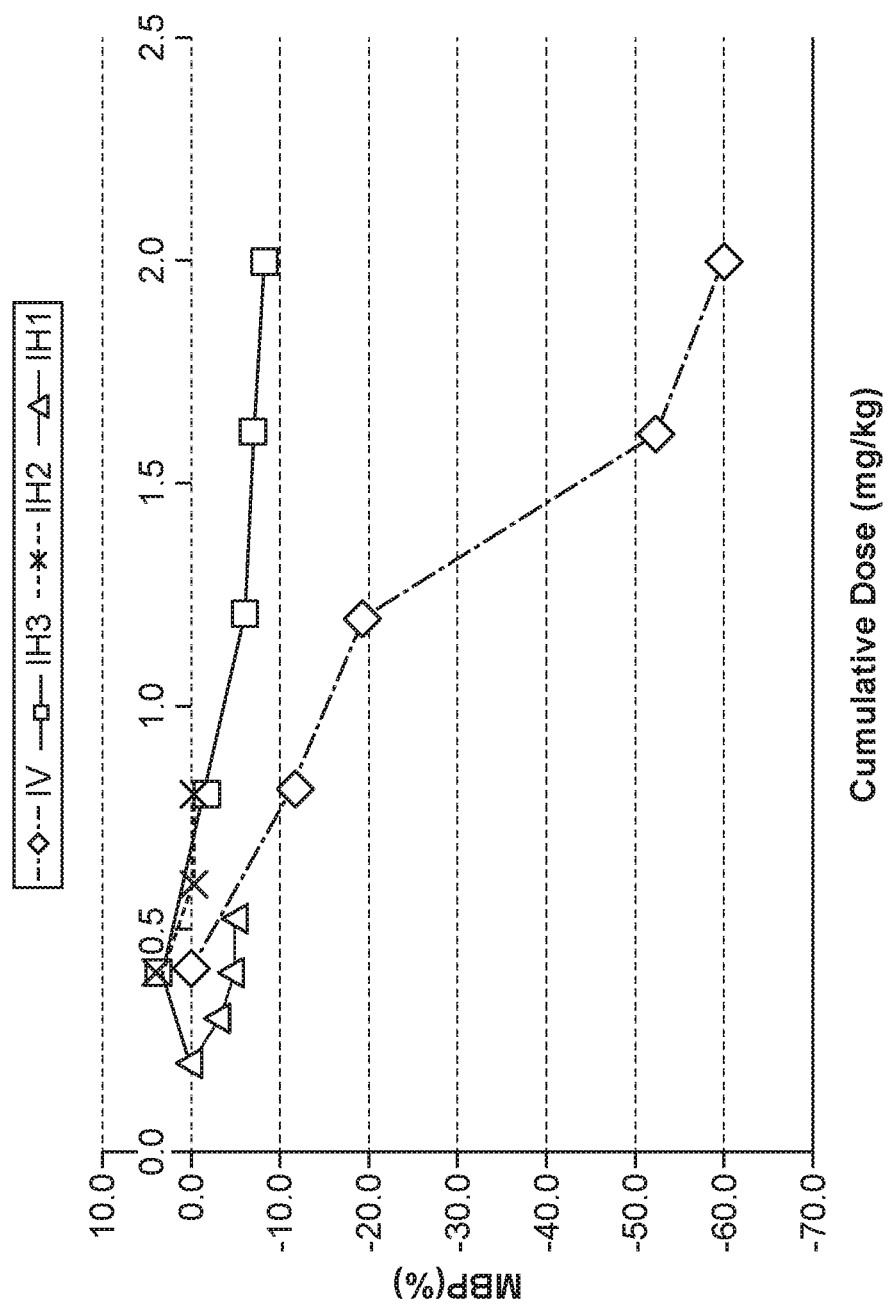
FIG. 4 depicts a plot of the effect of administration of flecainide on a subject's mean blood pressure after administration via intravenous injection or inhalation.
Figure 5:
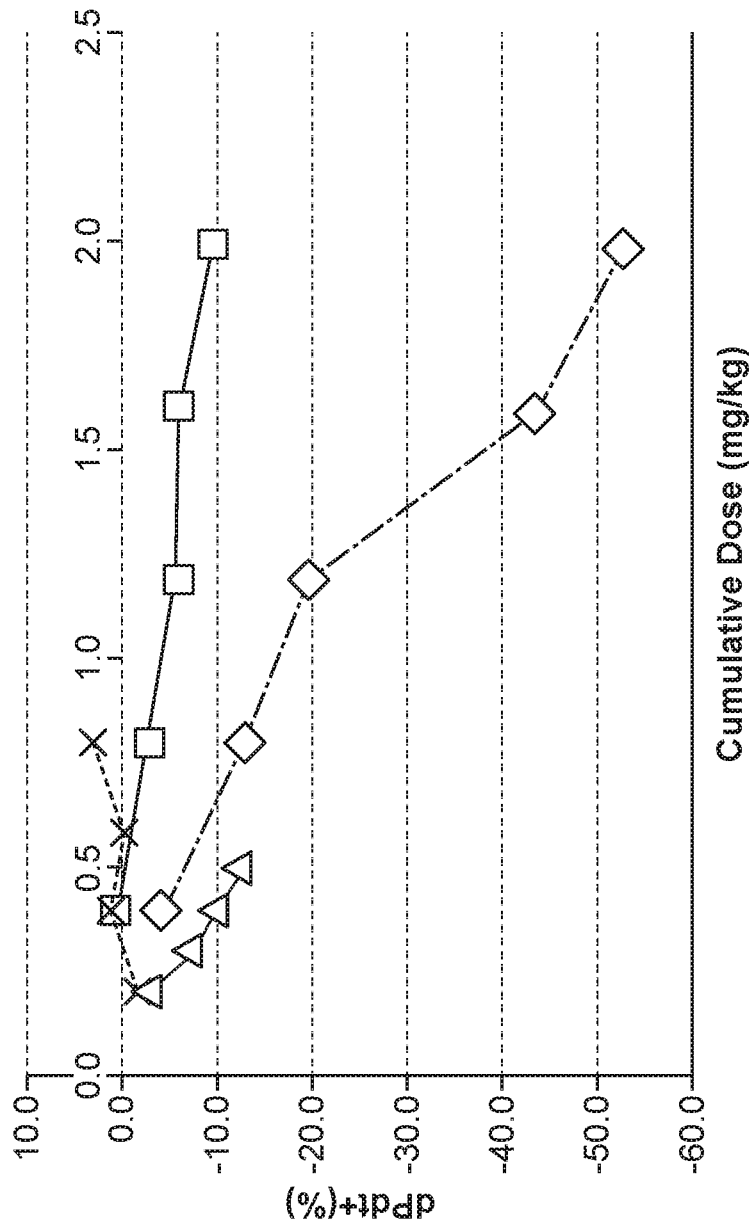
FIG. 5 depicts a plot of the effect of administration of flecainide on a subject's left ventricular pressure after administration via inhalation.
Figure 6:
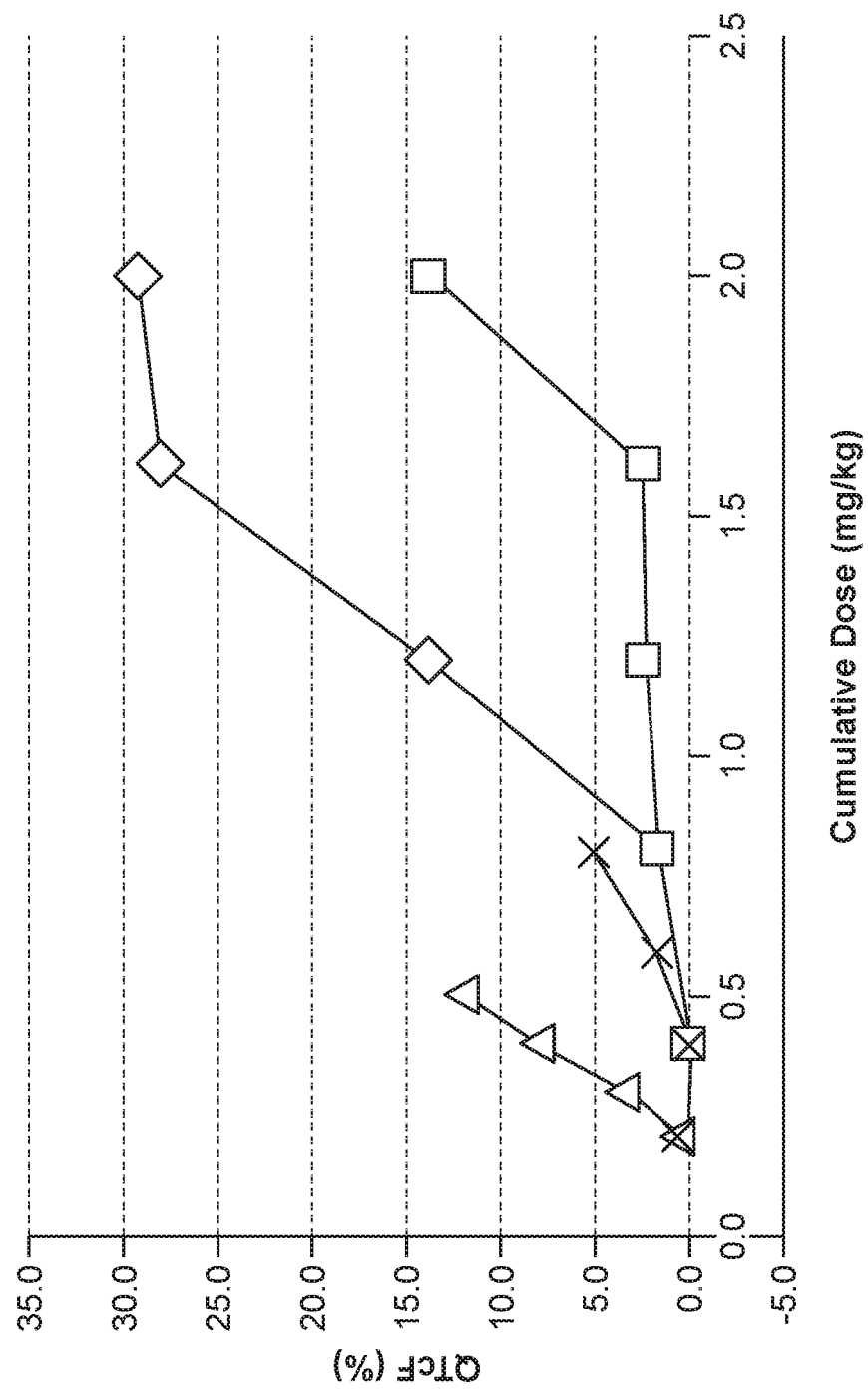
FIG. 6 depicts a plot of the effect of QTcf prolongation after administration of flecainide on a subject's left ventricular pressure after administration via inhalation.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

Accordingly, disclosed herein are compositions and methods for treating a heart arrhythmia comprising combining the treatment with an electronic monitoring system. Other features and advantages will be set forth in the description that follows, and in part will be apparent from the description or may be learned by practice of exemplary embodiments. The disclosure will be realized and attained by the compositions and methods particularly pointed out in the written description and claims thereof.

In some embodiments, the method can be directed to effective monitoring of subjects with AF through electronic means. In some cases, an electronic monitor can have an ability to record with a subject interface to an alert center. In some cases, an electronic monitor can have an ability to transmit with a subject interface to an alert center. In some cases, an electronic monitor can have an ability to record and transmit with a subject interface to an alert center. In some cases, an electronic monitor can have an ability to record without a subject interface to an alert center. In some cases, an electronic monitor can have an ability to transmit without a subject interface to an alert center. In some cases, an electronic monitor can have an ability to record and transmit without a subject interface to an alert center.

In some embodiments, the method can comprise physicians and/or qualified personnel reading the alert signals from subjects. In some cases, the method can comprise providing a subject with timely advice to self-administer CV medications to terminate an arrhythmia.

In some embodiments, the method can be directed to effectively shorten the time of arrhythmia, irrespective of whether it is symptomatic or asymptomatic, by a system where the subject monitoring compliments with the therapeutic administration of an antiarrhythmic. In some cases, the arrhythmia can be symptomatic. In some cases, the arrhythmia can be asymptomatic The present invention is directed to an electronic monitoring system that is either inserted or is subject enabled combined with a inhalation therapy that is self-administered either by advise from a monitoring center authorized medical personnel or by self-diagnosis of the arrhythmia.

The present invention is directed to administering by inhalation an effective amount of at least one antiarrhythmic agent to a subject in need thereof, wherein a cardiac score from a monitor implementing an arrhythmia detection algorithm is detected early in its onset and the subject's ability to self-administer the inhaled medication to enable a transition from an arrhythmic state to normal sinus rhythm in the subject within 0 seconds to 2 hours after completion of administration.

Unless otherwise indicated, some embodiments herein contemplate numerical ranges. When a numerical range is provided, unless otherwise indicated, the range includes the range endpoints. Unless otherwise indicated, numerical ranges include all values and sub ranges therein as if explicitly written out.

The singular forms "a", "an", and "the" can be used herein to include plural references unless the context clearly dictates otherwise. Accordingly, unless the contrary is indicated, the numerical parameters set forth in this application can be approximations that may vary depending upon the desired properties sought to be obtained by the present invention.

As used herein, the term "salt" is intended to include, but not be limited to, pharmaceutically acceptable salts. And the term "pharmaceutically acceptable salt" is intended to mean those salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates. The term "pharmaceutically acceptable" is intended to include, but not be limited to, mean that a component is not biologically or otherwise undesirable, e.g., the component may be incorporated into a pharmaceutical composition of the invention and administered to a subject as described herein without causing any significant undesirable biological effects or interacting in a deleterious manner with any of the other components of the composition in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Unless otherwise indicated, "aerosolizing a pharmaceutical composition" means at least about 90% by weight of the pharmaceutical composition is aerosolized. For example, "aerosolizing a pharmaceutical composition in less than 3 minutes" means at least 90% by weight of the pharmaceutical composition is aerosolized in less than 3 minutes.

Unless otherwise indicated, open terms for example "contain," "containing," "include," "including," and the like mean comprising.

Reference herein to "one embodiment," "one version," or "one aspect" shall include one or more such embodiments, versions or aspects, unless otherwise clear from the context.

As used herein, "tachycardia" means an arrhythmia in which the heart beat is too fast.

As used herein, the phrase "heart rhythm arrhythmia" means an arrhythmia in which the heart beat is irregular.

As used herein, the "amount of the at least one antiarrhythmic agent in blood in the coronary sinus of the heart" may be measured by extracting a sample from the coronary sinus of the heart by using a cannula. The amount of antiarrhythmic agent in the sample may then be determined by known means, such as bioanalytical techniques that employ analytical equipment such as LC-MS/MS. Thus, the amount of antiarrhythmic agent in the blood in the heart may be determined for any particular time.

As used herein, the terms "treating" and "treatment" refer to reduction in severity and/or frequency of symptoms, elimination of symptoms and/or underlying cause, reduction in likelihood of the occurrence of symptoms and/or underlying cause, and/or remediation of damage. Thus, "treating" a subject with an active agent as provided herein includes prevention of a particular condition, disease, or disorder in a susceptible individual as well as treatment of a clinically symptomatic individual.

As used herein, "nominal amount" refers to the amount contained within the unit dose receptacle(s) that can be administered.

As used herein, "effective amount" refers to an amount covering both therapeutically effective amounts and prophylactically effective amounts.

As used herein, a "therapeutically effective amount" of an active agent refers to an amount that is effective to achieve a desired therapeutic result. A therapeutically effective amount of a given active agent will typically vary with respect to factors such as the type and severity of the disorder or disease being treated and the age, gender, and weight of the subject.

Unless otherwise specified, the term "therapeutically effective amount" includes a "prophylactically effective amount," i.e., an amount of active agent that is effective to prevent the onset or recurrence of particular condition, disease, or disorder in a susceptible individual.

Pharmaceutical Composition

In some embodiments, a composition can comprise an antiarrhythmic agent. Examples of antiarrhythmic agents include, but are not limited to, class Ia (sodium channel blockers, intermediate association/dissociation), class Ib (sodium channel blockers, fast association/dissociation), class Ic (sodium channel blocker, slow association/dissociation), class II (beta blockers), class III (potassium channel blockers), class IV (calcium channel blockers), and class V (unknown mechanisms) antiarrhythmics.

Class Ia antiarrhythmics include, but are not limited to, quinidine, procainamide, and disopyramide. Class Ib antiarrhythmics include, but are not limited to, lidocaine, tocamide, phenyloin, moricizine, and mexiletine. Class Ic antiarrhythmics include, but are not limited to, flecainide, ajmaline, propafenone, and moricizine. Class II antiarrhythmics include, but are not limited to, propranolol, acebutolol, soltalol, esmolol, timolol, metoprolol, and atenolol. Class III antiarrhythmics include, but are not limited to, amiodarone, sotalol, bretylium, ibutilide, E-4031 (methanesulfonamide), vemakalant, and dofetilide. Class IV antiarrhythmics include, but are not limited to, bepridil, nitrendipine, amlodipine, isradipine, nifedipine, nicardipine, verapamil, and diltiazem. Class V antiarrhythmics include, but are not limited to, digoxin and adenosine.

The pharmaceutical composition can also include derivatives of the above antiarrhythmic pharmaceutical agents such as solvates, salts (e.g., acetate), solvated salts, esters, amides, hydrazides, N-alkyls, and/or N-amino acyls. In some cases, the pharmaceutical composition is a liquid pharmaceutical composition. Examples of ester derivatives include, but are not limited to, methyl esters, choline esters, and dimethylaminopropyl esters. Examples of amide derivatives include, but are not limited to, primary, secondary, and tertiary amides. Examples of hydrazide derivatives include, but are not limited to, N-methylpiperazine hydrazides. Examples of N-alkyl derivatives include, but are not limited to, N',N',N'-trimethyl and N',N'-dimethylaminopropyl succininimidyl derivatives of antiarrhythmic pharmaceutical agent methyl esters. Examples of N-aminoacyl derivatives include, but are not limited to, N-omithyl-, N-diaminopropionyl-, N-lysil-, N-hexamethyllysil-, and N-piperidine-propionyl- or N',N'-methyl-1-piperazine-propionyl-antiarrhythmic pharmaceutical agent methyl esters.

The pharmaceutical composition can comprise one or more antiarrhythmic pharmaceutical agents and, optionally, one or more pharmaceutically acceptable excipients. The pharmaceutically acceptable excipient can comprise lipids, metal ions, surfactants, amino acids, carbohydrates, buffers, salts, polymers, and the like, and combinations thereof. In some cases, the pharmaceutically acceptable excipient is water. In some cases, the pharmaceutically acceptable excipient is not water. Examples of lipids include, but are not limited to, phospholipids, glycolipids, ganglioside GMI, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. The pharmaceutically acceptable excipient can comprise one or more osmolality adjuster, such as sodium chloride. For instance, sodium chloride may be added to solutions to adjust the osmolality of the solution. In one or more embodiments, an aqueous composition consists essentially of the antiarrhythmic pharmaceutical agent, the osmolality adjuster, and water. The pharmaceutically acceptable can also comprise a buffer or a pH adjusting agent, typically a salt prepared from an organic acid or base. For example, the pharmaceutical compositions typically have a pH ranging from 3.5 to 8.0, such as from 4.0 to 7.5, 4.5 to 7.0, or 5.0 to 6.5. Representative buffers comprise organic acid salts of citric acid, lactic acid, ascorbic acid, gluconic acid, carbonic acid, tartaric acid, succinic acid, acetic acid, or phthalic acid, tris, trimethamine hydrochloride, or phosphate buffers. Thus, the buffers include citrates, phosphates, phthalates, and lactates. It may be desirable to add other pharmaceutically acceptable excipients to the pharmaceutical composition to improve particle rigidity, production yield, emitted dose and deposition, shelf-life, and subject acceptance. Such optional pharmaceutically acceptable excipients include, but are not limited to: coloring agents, taste masking agents, buffers, hygroscopic agents, antioxidants, and chemical stabilizers.

As noted above, the pharmaceutical composition may include one or more surfactants. For instance, one or more surfactants may be in the liquid phase with one or more being associated with (e.g., the pharmaceutical compositions may incorporate, adsorb, absorb, be coated with, or be formed by the surfactant) solid particles or particles of the composition. By "associated with" it is meant that the pharmaceutical compositions may incorporate, adsorb, absorb, be coated with, or be formed by the surfactant. Surfactants include, but are not limited to, fluorinated and nonfluorinated compounds, such as saturated and unsaturated lipids, nonionic detergents, nonionic block copolymers, ionic surfactants, and combinations thereof. Examples of ionic surfactants include, but are not limited to, sodium sulfosuccinate, and fatty acid soaps. Examples of buffers include, but are not limited to, tris or citrate. Examples of acids include, but are not limited to, carboxylic acids. Examples of carbohydrates include, but are not limited to, monosaccharides, disaccharides, and polysaccharides. For example, monosaccharides such as dextrose (e.g. anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (e.g., hydroxyethyl starch), cyclodextrins, and maltodextrins.

The pharmaceutical composition can comprise one or more antiarrhythmic pharmaceutical agents and, can include one or more additional active agents, for example, agents that may be delivered through the lungs. Additional active agents may comprise, for example, hypnotics and sedatives, psychic energizers, tranquilizers, respiratory drugs, anticonvulsants, muscle relaxants, anti-Parkinson agents (e.g. dopamine antagonists), analgesics, anti-inflammatories, anti-anxiety drugs (e.g. anxiolytics), appetite suppressants, antimigraine agents, muscle contractants, additional anti-infectives (e.g. antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The additional active agent, when administered by inhalation (e.g., as an aerosol), may act locally or systemically.

The amount of antiarrhythmic pharmaceutical agent in the pharmaceutical composition can vary. The amount of antiarrhythmic pharmaceutical agent(s) can be about 0.1% to 100% by weight of the total amount of the pharmaceutical composition. In some cases, the amount of antiarrhythmic pharmaceutical agent(s) is at least about 0.1% by weight of the total amount of the pharmaceutical composition, for example, at least about 0.1%, 0.2%, 0.3%, 0.4%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% by weight of the total amount of the pharmaceutical composition. In some cases, the amount of antiarrhythmic pharmaceutical agent(s) is about 0.1%-100% by weight of the total amount of the pharmaceutical composition, for example, about 0.1%-1%, 0.1%-5%, 0.1-10%, 0.1%-20%, 0.5%-1%, 0.5%-5%, 0.5%-10%, 0.5%-20%, 1%-5%, 1%-10%, 1%-20%, 5%-10%, 5%-20%, 10%-20%, 10%-30%, 20%-30%, 20%-40%, 30%-40%, 30%-50%, 40%-50%, 40%-60%, 50%-60%, 50%-70%, 60%-70%, 60%-80%, 70%-80%, 70%-90%, 80%-90%, 80%-95%, 90%-95%, 90%-99%, 90%-100%, 95%-99%, or 99%-100% by weight of the total amount of the pharmaceutical composition.

Method of Treatment

Described herein are methods of treating a condition in a subject pharmaceutical comprising delivering a pharmaceutical composition disclosed herein. The condition can be cardiac arrhythmia including, but not limited to, tachycardia, supraventricular, tachycardia (SVT), paroxysmal supraventricular tachycardia (PSVT), atrial fibrillation (AF), paroxysmal atrial fibrillation (PAF), permanent atrial fibrillation, persistent atrial fibrillation, atrial flutter, paroxysmal atrial flutter, and lone atrial fibrillation.

One aspect of embodiments disclosed herein is the surprising and unexpected rate at which the antiarrhythmic agents pass through the heart. While a skilled artisan might expect the rate to be too fast, modeling and empirical evidence indicates that the drug will not pass through the heart too fast. Thus, a therapeutic effect is achieved despite fast pass-through and despite only one pass-through at therapeutic levels Also described are methods to treat acute episodes of and/or chronic arrhythmias. In certain embodiments, the treating can comprise acute treatment after detection of cardiac arrhythmia.

Flecainide can be effective via IV at doses of 75-150 mg administered in a hospital or other suitable medical facility. The equilibration between arterial concentration and venous concentration can occur rapidly. On the other hand, inhalation can target the drug to the pulmonary vein that originates in the lung capillaries, and the left atrium where PAF originates. Inhalation can be started much earlier at onset rather than the subject waiting to go to the hospital for an IV. Alternatively, Flecainide can be also administered orally as a bolus of 300 mg (max per day) dose at one time to terminate PAF. Via this route, it can take an average of 100 minutes to terminate the PAF. Oral flecainide is 30-50% effective. Subjects who take this maximum dose are restricted until 24 hours to take any further antiarrhythmics. Conversely, an inhalation dose can be several orders of magnitude less than the oral dose, and thus permit repeat doses of flecainide.

The method of treatment via inhalation can result in a pulsatile pharmacokinetic profile and transient pharmacodynamic effect mimicking the effect of an IV. The method can delivers high drug concentrations that are safe and effective to the heart, while the distribution to the rest of the body results in the drug being diluted to sub-therapeutic levels. This method is the shortest route of delivery to the heart next to intracardial injection. This provides the convenience of self-administration like the "pill-in-the-pocket" approach, but the effectiveness and fast onset of action of an IV. Although the delivery of medications through the lung for systemic effect is not new, it was widely thought it wouldn't be effective to the heart, because of the fast passage of the drug through it, not having time to act on the target tissue. The PK/PD modeling and empirical evidence originating this invention shows that the drug exposure is sufficient for therapeutic effect at a much lower dose compared to other routes of administration. This method ensures dug concentrations in overall plasma are much lower than what is achieved by oral/IV hence minimizing drug-drug interactions and side effects.

The subject can be a mammal in need thereof, preferably such mammal is a human subject. Examples of subjects include, but are not limited to, pediatric subjects, adult subjects, and geriatric subjects. In some embodiments, the pharmaceutical composition is intended only as a treatment for rapid resolution of symptoms and is not taken as a preventative, i.e., when the subject is well, there is no need for drug-this makes the therapy more effective and safe due to sporadic or intermittent dosing, and focused on reducing disabling symptoms.

Unit doses of the pharmaceutical compositions may be contained in a container. Examples of containers include, but are not limited to, syringes, capsules, blow fill seal, blisters, vials, ampoules, bottles, or container closure systems made of metal, polymer (e.g., plastic, elastomer), glass, or the like. For instance, the vial may be a colorless Type I borosilicate glass ISO 6R 10 mL vial with a chlorobutyl rubber siliconized stopper, and rip-off type aluminum cap with colored plastic cover.

The unit dose can comprise at least about 0.1 mL of the pharmaceutical composition, for example, at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 65, 70, 75, 80, 85, 90, 95, or 100 mL of the pharmaceutical composition. The unit dose can comprise about 0.1-100 mL of the pharmaceutical composition, for example, about 0.1-0.2, 0.1-0.5, 0.1-1.0, 0.2-0.5, 0.2-1.0, 0.5-1.0, 0.5-1.5, 0.5-2.0, 0.5-3.0, 0.5-4.0, 0.5-5.0, 1.0-2.0, 1.0-3.0, 1.0-4.0, 1.0-5.0, 2.0-3.0, 2.0-4.0, 2.0-5.0, 3.0-5.0, 5-10, 10-20, 20-30, 30-40, 40-50, 50-60, 60-70, 70-80, 80-90, or 90-100 mL of the pharmaceutical composition. In some cases, the unit dose of the pharmaceutical composition ranges from about 2 ml to about 15 ml, such as from about 3 ml to about 10 ml, about 4 ml to about 8 ml, or about 5 ml to about 6 ml.

The container may be inserted into an aerosolization device (e.g., inhaler). The container may be of a suitable shape, size, and material to contain the pharmaceutical composition and to provide the pharmaceutical composition in a usable condition.

The compositions of the present invention may be made by any of the various methods and techniques known and available to those skilled in the art. For instance, a solution of antiarrhythmic pharmaceutical agent may be made using the following procedure. Typically, manufacturing equipment is sterilized before use. A portion of the final volume, e.g., 70%, of solvent, e.g., water for injection, may be added into a suitable container. Antiarrhythmic pharmaceutical agent may then be added. The antiarrhythmic pharmaceutical agent may be mixed until dissolved. Additional solvent may be added to make up the final batch volume. The batch may be filtered, e.g., through a 0.2 μm filter into a sterilized receiving vessel. Filling components may be sterilized before use in filling the batch into vials, e.g., 10 ml vials. As an example, the above-noted sterilizing may include the following. A 5 liter type 1 glass bottle and lid may be placed in an autoclave bag and sterilized at elevated temperature, e.g., 121° C., for 15 minutes, using an autoclave. Similarly, vials may be placed into suitable racks, inserted into an autoclave bag, and sterilized at elevated temperature, e.g., 121° C., for 15 minutes, using an autoclave. Also similarly, stoppers may be placed in an autoclave bag and sterilized at elevated temperature, e.g., 121° C., for 15 minutes, using an autoclave. Before sterilization, sterilizing filters may be attached to tubing, e.g., a 2 mm length of 7 mm×13 mm silicone tubing. A filling line may be prepared by placed in an autoclave bag and sterilized at elevated temperature, e.g., 121° C., for 15 minutes, using an autoclave. Sterilization may also be accomplished using electronic beams or gamma rays. The filling may also be conducted under laminar flow protection. The filling line may be unwrapped and placed into the receiving bottle. The sterilized vials and stoppers may be unwrapped under laminar flow protection. Each vial may be filled, e.g., to a target fill of 5 g, and stoppered. A flip off collar may be applied to each vial. The sealed vials may be inspected for vial leakage, correct overseals, and cracks.

As another example, an antiarrhythmic may be prepared by lyophilizing the antiarrhythmic to form a powder for storage. The powder is then reconstituted prior to use. This technique may be used when the antiarrhythmic is unstable in solution. The solvent for the solution to be lyophilized may comprise water. The solution may be excipient-free. For instance, the solution may be cryoprotectant-free. In one or more embodiments, a suitable amount (e.g., 30 mg per mL of final solution) of drug substance may be dissolved, e.g., in about the 75% of the theoretical total amount of water for injection under nitrogen bubbling. The dissolution time may be recorded and appearance may be evaluated. Then, the dilution to the final volume with water for injection (WFI) may be carried out. Final volume may be checked. Density, pH, endotoxin, bioburden, and content by UV may be measured both before and after sterile filtration.

The solution may be filtered before lyophilizing. For instance, a double 0.2 μm filtration may be performed before filling. The filters may be tested for integrity and bubble point before and after the filtration. Pre-washed and autoclaved vials may be aseptically filled using an automatic filling line to a target of 5 ml per vial and then partially stoppered. In process check for fill volumes may be done by checking the fill weight every 15 minutes. The lyophilizing is generally conducted within about 72 hours, such as within about 8 hours, or within about 4 hours, of the dissolving. In one or more embodiments, the lyophilizing can comprise freezing the solution to form a frozen solution. The frozen solution is typically held at an initial temperature ranging from about −40° C. to about −50° C., such as about −45° C. During the initial temperature period, the pressure around the frozen solution is typically atmospheric pressure. The initial temperature period typically ranges from about 1 hour to about 4 hours, such about 1.5 hours to about 3 hours, or about 2 hours. The lyophilizing may further comprise raising a temperature of the frozen solution to a first predetermined temperature, which may range from about 10° C. to about 20° C., such as about 15° C. The time for the heat ramp from the initial temperature to the first predetermined temperature generally ranges from about 6 hours to about 10 hours, such as about 7 hours to about 9 hours. During the first predetermined temperature period, the pressure around the solution typically ranges from about 100 μbar to about 250 μbar, such as about 150 μbar to about 225 μbar. The solution may be held at the first predetermined temperature for a period ranging from about 20 hours to about 30 hours, such as from about 24 hours. The lyophilizing may still further comprise raising a temperature of the solution to a second predetermined temperature, which may range from about 25° C. to about 35° C., such as about 30° C. During the second predetermined temperature period, the pressure around the frozen solution typically ranges from about 100 µbar to about 250 µbar, such as about 150 µbar to about 225 µbar. The solution may be held at the second predetermined temperature for a period ranging from about 10 hours to about 20 hours.

The lyophilization cycle may comprise a freezing ramp, e.g., from 20° C. to −45° C. in 65 minutes, followed by a freeze soak, e.g., at −45° C. for 2 hours. Primary drying may be accomplished with a heating ramp, e.g., from −45° C. to 15° C. in 8 hours, followed by a temperature hold, e.g., at 15° C. for 24 hours at a pressure of 200 µbar. Secondary drying may be accomplished with a heating ramp, e.g., from 15° C. to 30° C. in 15 minutes, followed by a temperature hold at 30° C. for 15 hours at a pressure of 200 µbar. At the end of the lyophilization cycle, the vacuum may be broken with sterile nitrogen, and the vials may be automatically stoppered. The water content of the lyophilized powder is typically less than about 7 wt %, such as less than about 5 wt %, less than about 4 wt %, less than about 3 wt %, less than about 2 wt %, or less than about 1 wt %. The powder is capable of being reconstituted with water at 25° C. and 1.0 atmosphere and with manual agitation, in less than about 60 seconds, such as less than about 30 seconds, less than about 15 seconds, or less than about 10 seconds. The powder typically has a large specific surface area that facilitates reconstitution. The specific surface area typically ranges from about 5 m$^2$/g to 20 m$^2$/g, such as about 8 m$^2$/g to 15 m$^2$/g, or about 10 m$^2$/g to 12 m$^2$/g. Upon reconstitution with water, the antiarrhythmic pharmaceutical agent solution typically has a pH that ranges from about 2.5 to about 7, such as about 3 to about 6.

The compositions of one or more embodiments of the present invention may be administered by inhalation. Moreover, the doses of composition that are inhaled can be much less than those administered by other routes and required to obtain similar effects. It may be due to the efficient targeting of the inhaled composition to the heart.

The dosage necessary and the frequency of dosing of the antiarrhythmic pharmaceutical agent depend on the composition and concentration of the antiarrhythmic pharmaceutical agent within the composition. In some cases, the dose is less than its normal intravenous dose. The pulmonary dose can be similar to intracardial doses.

Inhalation avoids the initial dilution of drug in the body as compared to intravenous or oral dosing. Inhalation also avoids first-pass metabolism, such as hepatic metabolism. For instance, calcium channel blockers, such as diltiazem, undergo significant hepatic metabolism when taken orally. Inhalation allows rapid delivery of the parent diltiazem compound to the heart as a bolus. Surprisingly, administration by inhalation of diltiazem via the inhalation route according to the present invention converted atrial fibrillation to normal sinus rhythm and reduced heart rate. Thus, administration by inhalation of diltiazem is useful for treating both atrial fibrillation and supraventricular tachycardia (SVT). In contrast, administration by IV of diltiazem is typically only used for converting SVT to normal sinus rhythm and in atrial fibrillation to reduce heart rate (not for converting to normal sinus rhythm). Inhalation also avoids red blood cell metabolism. For instance, the reduced dilution and short route associated with inhalation reduces red blood cell metabolism of esmolol. Inhalation may also avoid reduced blood pressure and fainting. For instance, IV administration of beta blockers, such as esmolol, and/or Class I antiarrhythmics such as flecainide, may reduce mean arterial blood pressure (MAP). Inhalation can allow rapid delivery of esmolol and/or flecainide without reducing MAP. As a result, inhalation of beta blockers and/or Class I antiarrhythmics may result in an MAP of 10 mm Hg to 20 mm Hg greater than the MAP resulting from IV administration of the same beta blocker or Class I antiarrhythmic. With inhaled cardiotherapy the drug is directed to the heart from the lungs as a bolus. So, the heart sees a high concentration. The drug is rapidly diluted as it passes through the heart, but the exposure time is sufficient for the desired pharmacological action. Once the drug passes through the heart, the concentration of the drug in the overall blood is below the therapeutic concentration and is considered ineffective and thus safer. The therapeutic window is the range of dosage of a drug or of its concentration in a bodily system that provides safe effective therapy. Anything below the minimum amount is sub-therapeutic and hence ineffective in that concentration. In view of the dilution, unwanted side effects are minimized.

The dose may be administered during a single inhalation or may be administered during several inhalations. The fluctuations of antiarrhythmic pharmaceutical agent concentration can be reduced by administering the pharmaceutical composition more often or may be increased by administering the pharmaceutical composition less often. Therefore, the pharmaceutical composition of one or more embodiments of the present invention may be administered from about four times daily to about once a month, such as about once daily to about once every two weeks, about once every two days to about once a week, and about once per week. The pharmaceutical composition can also be administered to the subject on an as-needed basis.

In some cases, the pharmaceutical composition in accordance with one or more embodiments of the invention may be administered from about 1 to about 4 times daily, such as from about 2 to about 3 times daily. In some cases, the antiarrhythmic may be administered daily. In some cases, the administration can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 times a month.

In some cases, an antiarrhythmic pharmaceutical agent or salt thereof can be administered at a dose of from about 1 mg to about 480 mg, from about 5 mg to about 480 mg, from about 10 mg to about 480 mg, from about 15 mg to about 480 mg, from about 20 mg to about 480 mg, from about 25 mg to about 480 mg, from about 30 mg to about 480 mg, from about 35 mg to about 480 mg, from about 40 mg to about 480 mg, from about 45 mg to about 480 mg, from about 50 mg to about 480 mg, from about 55 mg to about 480 mg, from about 60 mg to about 480 mg, from about 65 mg to about 480 mg, from about 70 mg to about 480 mg, from about 75 mg to about 480 mg, from about 80 mg to about 480 mg, from about 85 mg to about 480 mg, from about 90 mg to about 480 mg, from about 95 mg to about 480 mg, from about 100 mg to about 480 mg, from about 105 mg to about 480 mg, from about 110 mg to about 480 mg, from about 115 mg to about 480 mg, from about 120 mg to about 480 mg, from about 125 mg to about 480 mg, from about 130 mg to about 480 mg, from about 135 mg to about 480 mg, from about 140 mg to about 480 mg, from about 145 mg to about 480 mg, from about 150 mg to about 480 mg, from about 155 mg to about 480 mg, from about 160 mg to about 480 mg, from about 165 mg to about 480 mg, from about 170 mg to about 480 mg, from about 175 mg to about 480 mg, from about 180 mg to about 480 mg, from about 185 mg to about 480 mg, from about 190 mg to about 480 mg, from about 195 mg to about 480 mg, from about 200 mg to about 480 mg, from about 205 mg to about 480 mg, from about 210 mg to about 480 mg, from about 215 mg to about 480 mg, from about 220 mg to about 480 mg, from about 225 mg to about 480 mg, from about 230 mg to about 480 mg, from about 235 mg to about 480 mg, from about 240 mg to about 480 mg, from about 245 mg to about 480 mg, from about 250 mg to about 480 mg, from about 255 mg to about 480 mg, from about 260 mg to about 480 mg, from about 265 mg to about 480 mg, from about 270 mg to about 480 mg, from about 275 mg to about 480 mg, from about 280 mg to about 480 mg, from about 285 mg to about 480 mg, from about 290 mg to about 480 mg, from about 295 mg to about 480 mg, or from about 300 mg to about 480 mg.

In some cases, an antiarrhythmic pharmaceutical agent or salt thereof described herein can be administered at a dose of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179 180, 181, 182, 183, 184, 184, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, or 480 mg.

In some exemplary embodiments, a daily dosage of an antiarrhythmic pharmaceutical agent (e.g. flecainide) can range from about 0.1 mg to about 600 mg, such as about 0.5 mg to about 500 mg, about 1 mg to about 400 mg, about 2 mg to about 300 mg, and about 3 mg to about 200 mg.

For treating a subject suffering from arrhythmia, the amount per dose of antiarrhythmic pharmaceutical agent (e.g. flecainide) administered may be an amount that is effective to treat the arrhythmia. The amount of antiarrhythmic pharmaceutical agent (e.g. flecainide) for the treatment of arrhythmia can be at least about 0.001 mg/kg, such as at least about 0.001 mg/kg, 0.002 mg/kg, 0.003 mg/kg, 0.004 mg/kg, 0.005 mg/kg, 0.01 mg/kg, 0.02 mg/kg, 0.04 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, or 6 mg/kg. The amount of antiarrhythmic pharmaceutical agent (e.g. flecainide) for the treatment of arrhythmia can range from about 0.001 mg/kg to 6 mg/kg, such as from about 0.001 mg/kg to about 0.01 mg/kg, from about 0.01 mg/kg to about 0.05 mg/kg, from about 0.05 mg/kg to about 0.1 mg/kg, from about 0.1 mg/kg to about 0.2 mg/kg, from about 0.1 mg/kg to about 0.5 mg/kg, from about 0.1 mg/kg to about 1 mg/kg, from about 0.1 mg/kg to about 2 mg/kg, from about 0.1 mg/kg to about 3 mg/kg, from about 0.3 mg/kg to about 1 mg/kg, from about 0.3 mg/kg to about 2 mg/kg, from about 0.3 mg/kg to about 3 mg/kg, from about 0.5 mg/kg to about 1 mg/kg, from about 0.5 mg/kg to about 2 mg/kg, from about 0.5 mg/kg to about 3 mg/kg, from about 0.5 mg/kg to about 6 mg/kg, from about 0.7 mg/kg to about 1 mg/kg, from about 0.7 mg/kg to about 2 mg/kg, from about 0.7 mg/kg to about 4 mg/kg, from about 0.7 mg/kg to about 6 mg/kg, from about 1 mg/kg to about 2 mg/kg, from about 1 mg/kg to about 4 mg/kg, from about 1 mg/kg to about 6 mg/kg, from about 2 mg/kg to about 3 mg/kg, from about 2 mg/kg to about 4 mg/kg, from about 2 mg/kg to about 6 mg/kg, or from about 3 mg/kg to about 6 mg/kg.

The amount of antiarrhythmic pharmaceutical agent (e.g. flecainide) for the treatment of arrhythmia can be at least about 0.1 mg, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, or 150 mg. The amount of antiarrhythmic pharmaceutical agent (e.g. flecainide) for the treatment of arrhythmia can range about 0.01-150 mg, such as about 0.1-150, 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 mg. For example, the amount of antiarrhythmic pharmaceutical agent (e.g. flecainide) for the treatment of arrhythmia can range about from 0.1 to about 5 mg.

In some instances, an antiarrhythmic can be administered as a unit dose. In some cases, a unit dose can be a dose of from about 0.1 mg to about 100 mg or greater of an antiarrhythmic pharmaceutical agent to the lung in a single inhalation. The above described phospholipid hollow and/or porous dry powder particles allow for doses of about 5 mg or greater, often greater than about 10 mg, sometimes greater than about 15 mg, sometimes greater than about 20 mg, sometimes greater than about 25 mg, sometimes greater than about 30 mg, sometimes greater than about 35 mg, sometimes greater than about 40 mg, sometimes greater than about 45 mg, sometimes greater than about 50 mg, sometimes greater than about 55 mg, sometimes greater than about 60 mg, sometimes greater than about 65 mg, sometimes greater than about 70 mg, sometimes greater than about 75 mg, sometimes greater than about 80 mg, sometimes greater than about 85 mg, sometimes greater than about 90 mg, sometimes greater than about 95 mg, or sometimes greater than about 100 mg, to be delivered in a single inhalation and in an advantageous manner. Alternatively, a dosage may be delivered over two or more inhalations, such as at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 inhalations. A dosage may also be delivered over 1 to 100 inhalations, such as 1-3, 1-4, 1-5, 1-6, 1-10, 1-20, 1-50, 1-80, 1-100, 2-5, 2-6, 2-10, 2-20, 2-50, 2-100, 5-10, 5-20, 5-50, 5-100, 10-20, 10-50, 10-100, 20-50, 20-100, or 50-100 inhalations. For example, a 10 mg dosage may be delivered by providing two unit doses of 5 mg each, and the two unit doses may be separately inhaled. In certain embodiments, the overall dose of the antiarrhythmic pharmaceutical agent ranges from 0.1 mg to 200 mg, such as 0.5 mg to 150 mg, or 1 mg to 100 mg. In some instances the antiarrhythmic agent can be administered as-needed titrating the dosage to effect.

The concentration of antiarrhythmic pharmaceutical agent (e.g. flecainide) for the treatment of arrhythmia can be at least about 0.1 mg/mL, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150 mg/mL. For example, the concentration of antiarrhythmic pharmaceutical agent (e.g. flecainide) for the treatment of arrhythmia can be at least about 30 mg/mL in an acetate buffer. The concentration of antiarrhythmic pharmaceutical agent (e.g. flecainide) for the treatment of arrhythmia can range about 0.1-150 mg/mL, such as about 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 mg/mL. For example, the concentration of antiarrhythmic pharmaceutical agent (e.g. flecainide) for the treatment of arrhythmia can range about 30-50 mg/mL in an acetate buffer.

The present invention can be directed to a method of self-diagnosing and treating cardiac arrhythmia. The method can comprise self-diagnosing cardiac arrhythmia by detecting at least one of shortness of breath, heart palpitations, and above normal heart rate. The method also can comprise self-administering by inhalation an effective amount of at least one antiarrhythmic pharmaceutical agent within two hours, such as within one hour, 30 minutes, or within 15 minutes, of the self-diagnosing. In some cases, the subject can self-titrate. For example, the subject can self-administer, e.g., by using an inhaler, until disabling symptoms disappear. In some cases, the self-administering continues until the subject no longer feels heart palpitations.

The time for onset of action is also typically short. For instance, the subject may have normal sinus rhythm within 20 minutes of initiating the administering, such as within 15 minutes, within 10 minutes, or within 5 minutes of initiating the administering. The rapid onset of action is advantageous because the longer a subject has had arrhythmia, the longer it typically takes to convert the subject to normal sinus rhythm. In some embodiments, the method of the present invention allows the subject to avoid other therapies, such as ablation and/or electrical cardioversion. In other embodiments, the method of the present invention is used in combination with other therapies, such as before or after electrical cardioversion and/or ablation therapy.

Device

The pharmaceutical composition may be delivered by an inhaler as described in WO 99116420, by a metered dose inhaler as described in WO 99116422, by a liquid dose instillation apparatus as described in WO 99116421. Inhalers impart energy into a liquid pharmaceutical composition to aerosolize the liquid, and to allow delivery to the pulmonary system, e.g., the lungs, of a subject. An inhaler can comprise a liquid delivery system, such as a container having a reservoir that contains a liquid pharmaceutical composition. The liquid pharmaceutical composition generally can comprise an active agent that is either in solution or suspended within a liquid medium.

In one type of inhaler, generally referred to as a jet inhaler, compressed gas is forced through an orifice in the container. The compressed gas forces liquid to be withdrawn through a nozzle, and the withdrawn liquid mixes with the flowing gas to form aerosol droplets. A cloud of droplets is then administered to the subject's respiratory tract. The compressed gas can be compressed air or compressed oxygen.

In another type of inhaler, generally referred to as a vibrating mesh inhaler, energy, such as mechanical energy, vibrates a mesh. This vibration of the mesh aerosolizes the liquid pharmaceutical composition to create an aerosol cloud that is administered to the subject's lungs. The vibrating mesh inhaler can comprise a metal vibrating mesh. In some cases, iron constitutes at least about 30% weight, such as 30%, 40%, 50%, 60%, 70%, 80%, or 90% of the metal vibrating mesh. An inhaler of the vibrating mesh type, such as one that that forms droplets without the use of compressed gas, such as the Aeroneb® Pro can provide unexpected improvement in dosing efficiency and consistency. By generating fine droplets by using a vibrating perforated or unperforated membrane, rather than by introducing compressed air, the aerosolized pharmaceutical formulation can be introduced without substantially affecting the flow characteristics. In addition, the generated droplets when using an inhaler of this type are introduced at a low velocity, thereby decreasing the likelihood of the droplets being driven to an undesired region.

In still another type of inhaler, generally referred to as an ultrasonic wave inhaler, ultrasonic waves or ultrasonic agitations are generated to directly vibrate and aerosolize the pharmaceutical formulation.

Alternatively or additionally, the pharmaceutical composition may be in a liquid form and may be aerosolized using an inhaler as described in WO 2004/071368, which is herein incorporated by reference in its entirety, as well as U.S. Published application Nos. 2004/0011358 and 2004/0035413, which are both herein incorporated by reference in their entireties. Other examples of inhalers include, but are not limited to, the Aeroneb Go or Aeroneb® Pro nebulizers, available from Aerogen Ltd. of Galway, Ireland; the PARI eFlow and other PARI nebulizers available from PARI Respiratory Equipment, Inc. of Midlothian, Va.; the Lumiscope® Nebulizer 6600 or 6610 available from Lumiscope Company, Inc. of East Brunswick, N.J.; and the Omron NE-U22 available from Omron Healthcare, Inc. of Kyoto, Japan.

The inhaler has the ability to rapidly deliver the aerosol at a rate that assures availability of a bolus dose in the heart. The inhaler can aerosolize the pharmaceutical composition in short amount of time. In some cases, the inhaler can aerosolize the pharmaceutical composition (e.g. at least 30 mg of flecainide) in less than about 20 minutes, such as less than about 10 seconds, 20 seconds, 30 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. For example, the inhaler can aerosolize at least 30 mg of flecainide in less than 3 minutes. In some cases, the inhaler can aerosolize the pharmaceutical composition in about 10 seconds to 20 minutes, such as about 10-20 seconds, 10-30 seconds, 10 seconds to 1 minute, 10 seconds to 2 minute, 10 seconds to 3 minute, 20-30 seconds, 20 seconds to 1 minute, 20 seconds to 2 minute, 20 seconds to 3 minute, 30 seconds to 1 minute, 30 seconds to 2 minutes, 30 seconds to 3 minutes, 1-2 minutes, 1-5 minutes, 2-20 minutes, 2-10 minutes, 2-5 minutes, 5-20 minutes, 5-10 minutes, or 10-20 minutes. For example, the inhaler can aerosolize at least 30 mg of flecainide in about 30 seconds to 3 minutes.

One or more embodiments of the present invention may be used in conjunction with liquid dose instillation or LDI techniques as disclosed in, for example, WO 99116421, which is incorporated herein by reference in its entirety. Liquid dose instillation involves the direct administration of a formulation to the lung. With respect to LDI the formulations are preferably used in conjunction with partial liquid ventilation or total liquid ventilation. Moreover, one or more embodiments of the present invention may further comprise introducing a therapeutically beneficial amount of a physiologically acceptable gas (such as nitric oxide or oxygen) into the pharmaceutical micro-dispersion prior to, during or following administration.

The pharmaceutical composition of one or more embodiments of the present invention typically has improved emitted dose efficiency. Accordingly, high doses of the pharmaceutical composition may be delivered using a variety of aerosolization devices and techniques. The emitted dose (ED) of the particles of the present invention may be greater than about 30%, such as greater than about 40%, greater than about 50%, greater than about 60%, or greater than about 70%.

The present invention may involve a follow-up inhalation if no cardioversion occurs after an initial inhalation. Typically, if no cardioversion occurs within 30 minutes of the initial inhalation, the follow-up dosage is higher or the same as the initial dosage. The dosing may be guided by how the subject feels.

Electronic Systems

In some cases, an electronic system can be used to monitor an occurrence or incidence of atrial fibrillation, and administer treatment to a subject in need thereof. Exemplary embodiments of a system can include an electronic monitoring chip, an electronic monitoring device, and an inhaler. Each component of a system can be in communication with any or all components of the system. The terms "communication," "communicated," "in communication with," "transmission," and "receiving" can refer to electronic exchange or communication between devices. In some instances, the exchange can occur though a wired connection between the devices such as through the use of a USB cord or fiber optic connection. In some instances, the exchange can occur through a wireless connection between the devices. In some cases, a wireless signal can be sent through a mobile data network such as a 4G LTE or 3G data signal. In some cases, a wireless signal can be sent through a Bluetooth connection. In some cases, a wireless signal can be sent through a Wi-Fi connection. In some cases, a wireless signal can be sent through an infra-red data association link.

An electronic monitoring chip can be inserted or implanted into a subject, and be used to detect a signal that correlates to an ECG in the subject. Alternatively, or in addition to insertion, an electronic monitoring chip can be worn by a subject. In some cases, an electronic monitoring device can be a component of a wearable electronic device such as a watch, ankle bracelet, and the like. An electronic monitoring chip can be in communication with an electronic monitoring device, an inhaler, or both. In some exemplary embodiments, a communication can be a wireless communication.

An electronic monitoring device may include but not limited to hand held heart monitors, hand held ECG monitors, Bluetooth App-Enabled Monitors, and the like. In some cases, a smartphone can be used as an electronic monitoring device. Such a device can include an application that can allow a smartphone to communicate with a that have the ability to transmit the cardiac readings to a monitoring center and/or chips and loop recorders inserted into a subject for the purpose of diagnosis and pharmacological intervention.

In some cases, an electronic monitoring device can include means to instruct a subject, or other personnel. In some cases, an audible source, a tactile source, and/or a visual source can be included. In some cases, an audible source can be a device producing sound. In some embodiments an audible source can be one or more speakers. A tactile source can comprise a tactile sensor. In some embodiments, a tactile sensor can detect a stimuli resulting from mechanical stimulation, or temperature. A visual source can be a light, multiple lights, gauge, display or the like. For example, in an exemplary embodiment the visual source can be a screen on a handheld device.

In some cases, an inhaler as described herein can be employed as part of a system. In some instances, the inhaler can be in communication with an electronic monitoring system. An electronic monitoring system can be used to direct administration of a pharmaceutical composition by an inhaler in communication therewith. In some cases, an electronic device can allow administration of the pharmaceutical composition by the inhaler. For example, an electronic device may allow administration when an electronic monitoring chip detects an incidence of atrial fibrillation. In some cases, an electronic device can prevent administration of the pharmaceutical composition by the inhaler. For example, an electronic device may prevent administration when an electronic monitoring chip does not detect an incidence of atrial fibrillation; when a healthcare professional overrides an administration; or when administration is deemed unsafe.

In some cases, an inhaler can contain visual, audible, or tactile sources as described above.

Furthermore, a system described herein can perform self-monitoring checks to detect and alert of potential fault conditions.

In some instances, dosing may be guided by a portable ECG. For instance, the dosing may be guided by a heart monitoring device (e.g. Holter monitor). In another version, the pharmaceutical composition is administered prophylactically to a subject who is likely to develop an arrhythmia. For example, a subject who has a history of arrhythmias can be prophylactically treated with a pharmaceutical composition comprising antiarrhythmic pharmaceutical agent to reduce the likelihood of developing an arrhythmia. The pharmaceutical composition may be administered to a subject in any regimen which is effective to prevent an arrhythmia. Illustrative prophylactic regimes include administering an antiarrhythmic pharmaceutical agent as described herein 1 to 21 times per week. In some cases, an overall cumulative arrhythmic burden is controlled by monitoring.

In some cases, a result can be communicated to a healthcare profession. A healthcare professional can include a physician, a paramedic, a nurse, and the like. A system or device herein can be employed by a healthcare professional in a number of settings, including, but not limited to, a hospital, hospice, clinic, office, ambulance, nursing home, and the like. In some cases, a result can be communicated to a non-healthcare professional. In some cases, a result can be communicated to a monitoring center. In some instances, a monitoring center can contact the subject between 0 secs to 60 mins for the purpose of communicating the diagnosis and ascertaining the subject's ability to self-administer the dose of the inhaled antiarrhythmic.

Employment of a system described herein can produce an overall management of arrhythmia. This can result in fewer hospital visits, ER visits and extended hospitalizations.

In some cases, a system or component thereof can be capable of communicating with doctors, health providers, health provider organizations or their computerized systems to notify that the arrhythmia has been detected, the doses and nature of the pharmacological agent delivered, and the response of the arrhythmia to the pharmacological dose.

A method can comprise administering to free breathing subjects by way of an aerosol generator device and/or system for administration of aerosolized medicaments such as those disclosed in U.S. Published Application Nos. 20050235987, 20050211253, 20050211245, 20040035413, and 20040011358, the disclosures of which are incorporated herein by reference in their entireties.

Also disclosed herein are kits for treating cardiac arrhythmias. For instance, the kit may include an aerosolization device and/or a container, e.g., unit dose receptacle, containing aerosolizable antiarrhythmic pharmaceutical agent (e.g., flecainide), for example, as a liquid or dry powder. The kit may further comprise a package, such as a bag, that contains the aerosolization device and/or the container. The kit may further comprise instructions for the aerosolization device and/or the container.

EXAMPLES

Example 1: Evaluation of Rate of Aerosolization in Different Buffer and Solution Systems The methods disclosed herein relate to the nebulization of flecainide acetate solution for treating AF, PAF and PSVT, e.g. when they manifest as acute episodes. It can be essential that the inhaler has the ability to rapidly deliver the aerosol at a rate that assures availability of a bolus dose in the heart. When a pharmaceutical composition of flecainide around 30-40 mg/mL in an acetate buffer is used, one would require 1 to 2.0 ml of the drug to be dosed within 1-3 minutes to be effective.

The time required for aerosolizing solutions with different buffer and excipient systems were tested and measured using an Omron MicroAir device (Table 1). The aerosolization time for aerosolizing 0.3 mL of each solution was recorded. The device used was a vibrating mesh that is made of a Titanium-nickel alloy.

TABLE 1

Evaluation of rate of aerosolization in different buffer and solution systems using the Omron MicroAir

| Sample | Aerosolization time (s) (0.3 mL) | Rate (mL/min) |
|---|---|---|
| 0.9% sodium chloride (control) | 27 | 0.67 |
| 30 mM acetate | 34 | 0.53 |
| 22.5 mM acetate | 27 | 0.67 |
| 15 mM acetate | 30 | 0.60 |
| 7.5 mM acetate | 31 | 0.58 |
| 40 mg/mL solution | 281 | 0.06 |
| 30 mg/mL solution | 260 | 0.07 |
| 20 mg/mL solution | 213 | 0.08 |
| 10 mg/mL solution | 131 | 0.14 |
| 40 mg/mL solution | 281 | 0.06 |
| 30 mg/mL solution (22.5 mM acetate) | 224 | 0.08 |
| 20 mg/mL solution (15 mM acetate) | 182 | 0.10 |
| 10 mg/mL solution (7.5 mM acetate) | 134 | 0.13 |

Example 2: Assessment of Different Inhalers with Flecainide Acetate (FA) Solution Different inhalers were then tested to assess compatibility of material to the different materials of construction and different types of inhalers (Table 2).

TABLE 2

Assessment of different inhalers with flecainide acetate (FA) solution at 30 mg/ml.

| Device | Device Type | Material of construction | Solution | Average (mL/min) | St dev (mL/min) |
|---|---|---|---|---|---|
| Voyager | Vibrating Mesh | Not known | 30 mg/mL FA | 0.16 | 0.01 |
| | | | Saline | 0.29 | 0.01 |
| AeroNeb Solo | | Nickel-Palladium | 30 mg/mL FA | 0.06 | 0.01 |
| | | | Saline | 0.55 | 0.01 |
| Pari eRapid | | Stainless steel | 30 mg/mL FA | 0.61 | 0.06 |
| | | | Saline | 0.84 | 0.09 |
| Mini-Breeze | Ultrasonic | No mesh | 30 mg/mL FA | 0.13 | 0.04 |
| | | | Saline | 0.29 | 0.02 |
| Lumiscope | | | 30 mg/mL FA | 0.85 | 0.03 |
| | | | Saline | 1.08 | 0.07 |
| CompXP | Compressed air | | 30 mg/mL FA | 0.14 | 0.02 |
| | | | Saline | 0.14 | 0.01 |
| Trek S (PART) | | | 30 mg/mL FA | 0.34 | 0.01 |
| | | | Saline | 0.26 | 0.01 |

The above results showed that a 30-40 mg dose of flecainide can be effectively delivered using the Pari e-rapid or Lumiscope inhalers in less than 2 minutes. The Trek S from PARI was able to deliver the same dose in about 3 minutes.

Example 3: Assessment of Flecainide Acetate (FA) Efficacy Using an Electronic Monitoring System An exemplary smart phone app was installed on a smartphone in order to monitor the efficacy of FA at ceasing incidence of atrial fibrillation. The smartphone app allowed for communication between the smart phone and an electronic monitoring chip used to produce an ECG.

Figure 7:
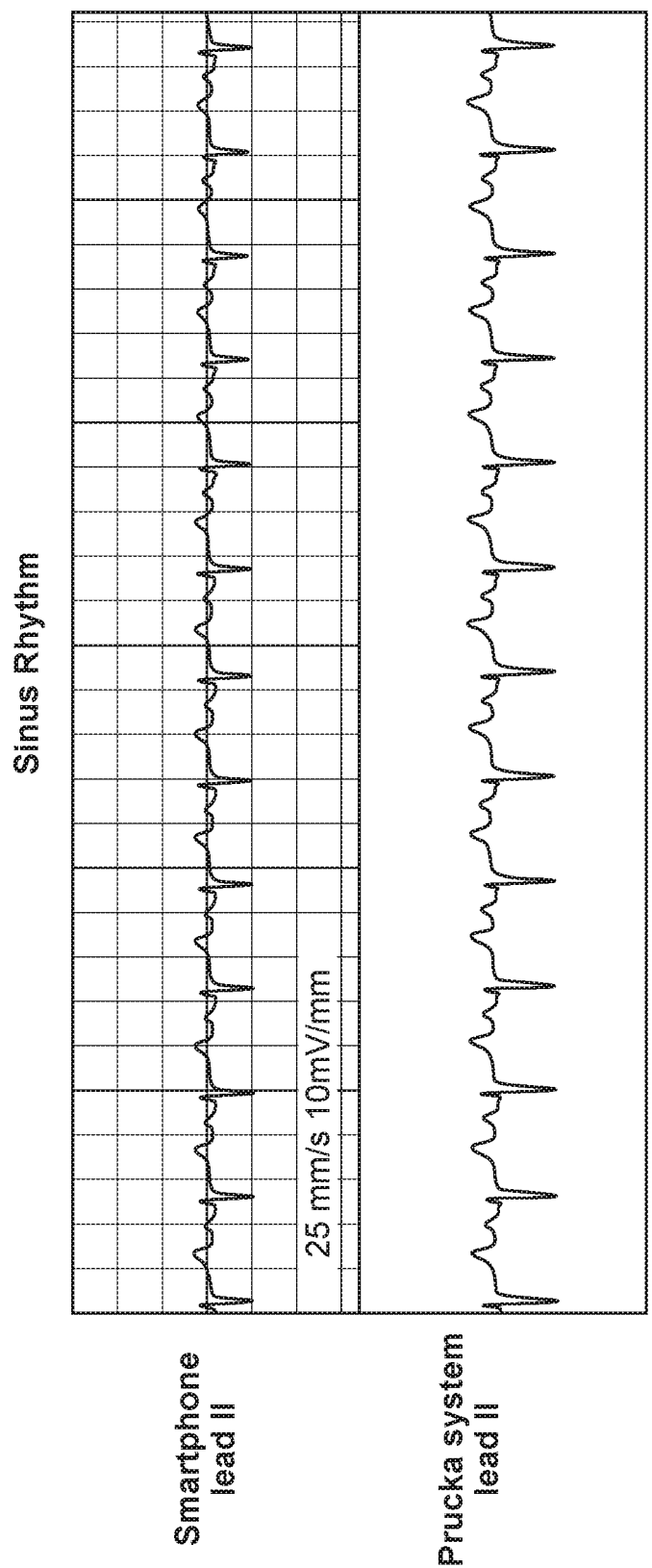
FIG. 7 depicts an exemplary plot of sinus rhythm using a smart phone as a novel electronic monitoring device as compared to a Prucka System II.

FIG. 7 depicts an exemplary ECG produced from a smartphone as compared to a Prucka System in an animal in sinus rhythm. The traces show excellent correlation between the two devices.

Figure 8:
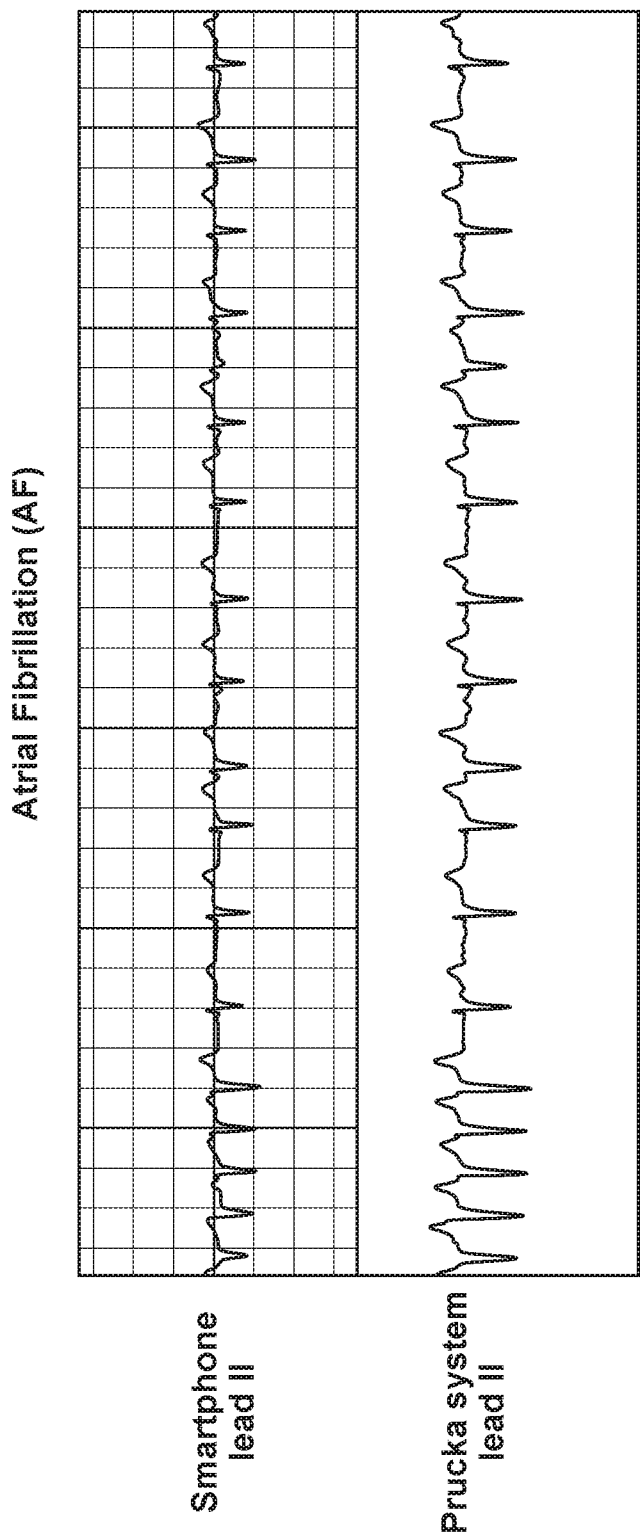
FIG. 8 depicts an exemplary plot of Atrial Fibrillation using a smart phone as a novel electronic monitoring device as compared to a Prucka System II.

FIG. 8 depicts an exemplary ECG produced from a smartphone as compared to a Prucka System in an animal displaying atrial fibrillation. Again, the traces show excellent correlation between the two devices.

Figure 9:
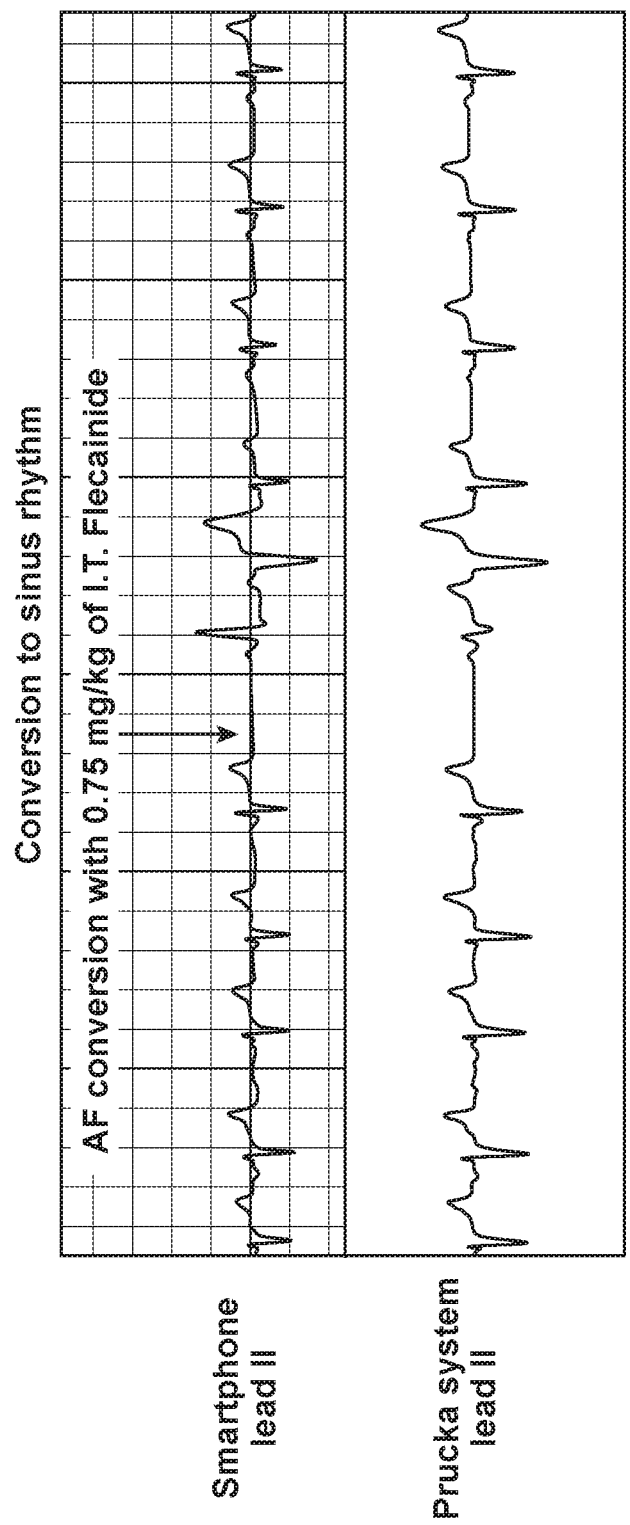
FIG. 9 depicts an exemplary plot of a treatment of Atrial Fibrillation with flecainide using a smart phone as a novel electronic monitoring device as compared to a Prucka System II.
Figure 10:
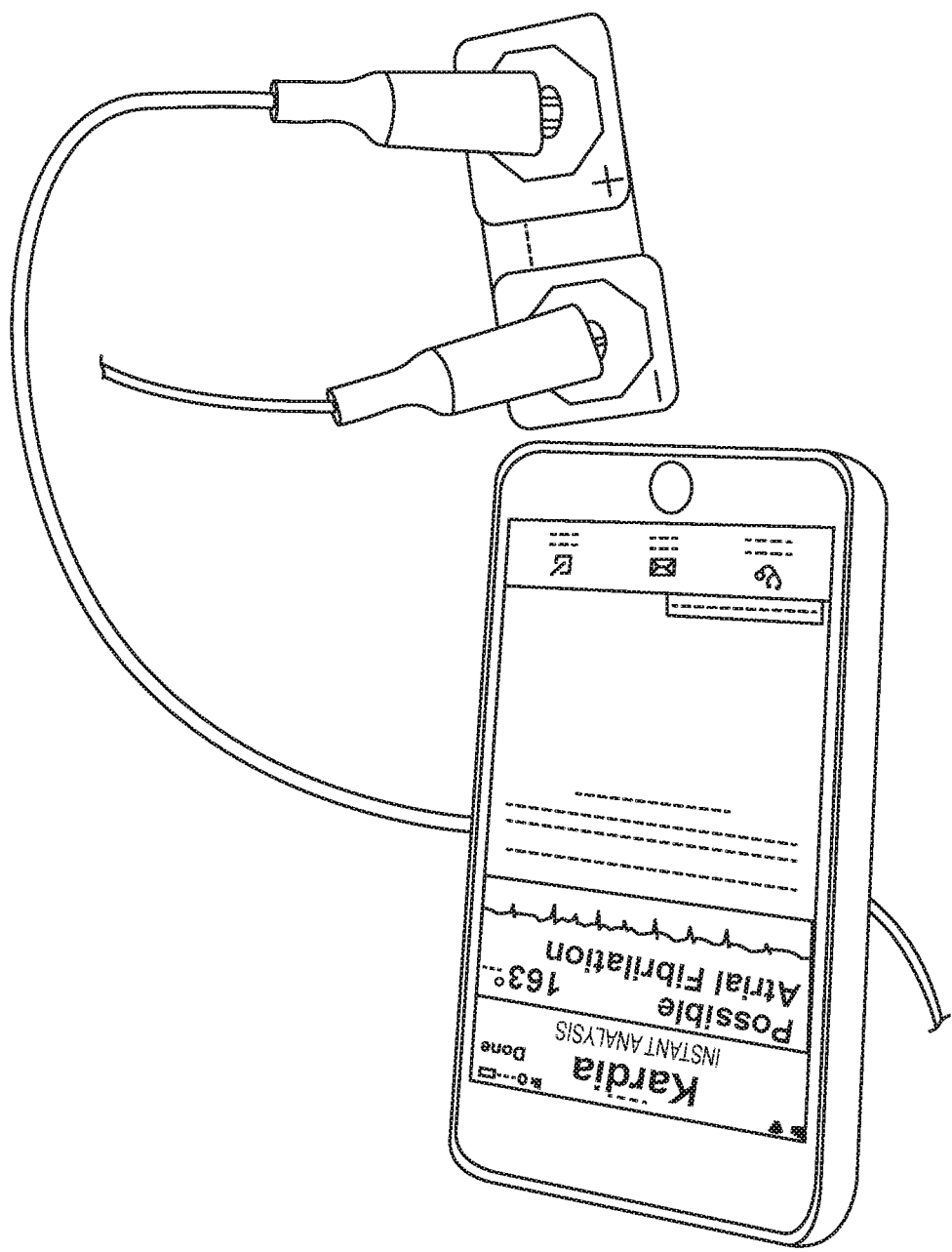
FIG. 10 depicts an exemplary smart phone application allowing the smartphone to be used as an electronic monitoring device
Figure 11:
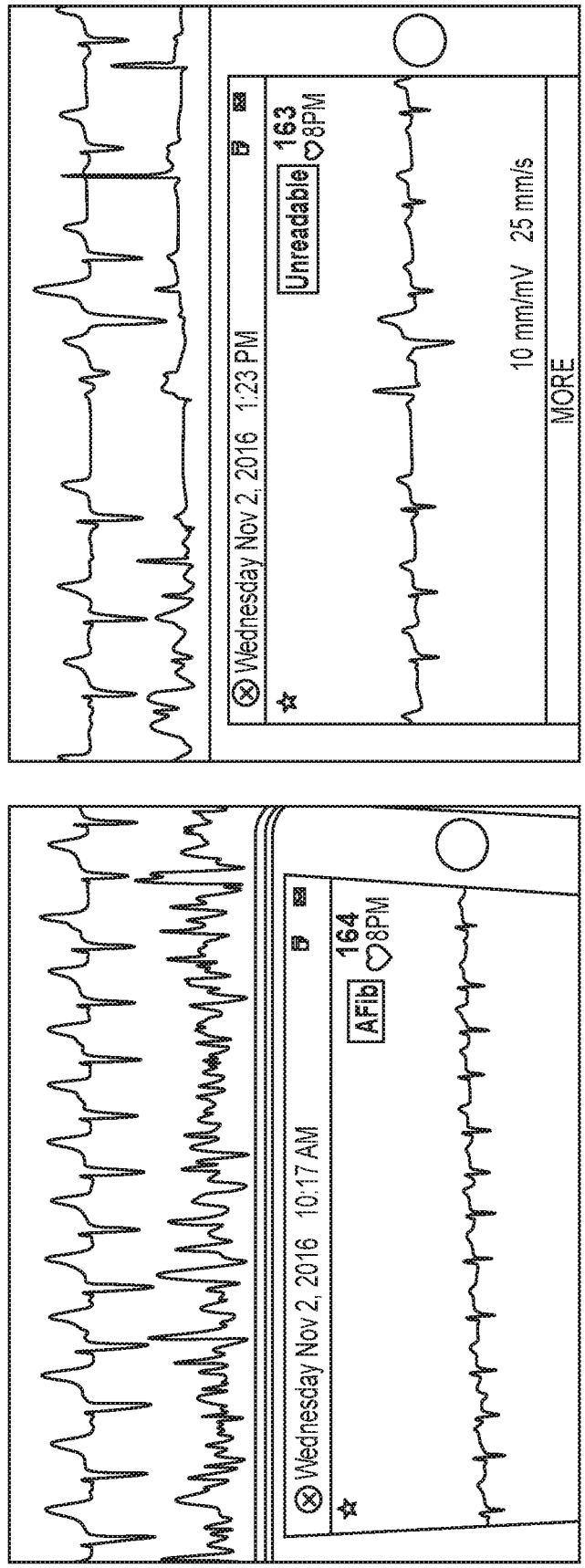
FIG. 11 depicts a smart phone in use as an electronic monitoring device to monitor treatment of Atrial Fibrillation with flecainide.

The smart phone device was then used to monitor the treatment efficacy of an intra-tracheal administration of 0.75 mg/kg flecainide in treating atrial fibrillation. FIG. 9 depicts an exemplary ECG produced from a smartphone as compared to a Prucka System in an animal displaying atrial fibrillation. Again, the traces show excellent correlation between the two devices. Each device shows a return to sinus rhythm upon administration. FIG. 10 depicts the actual employment of the smart phone to monitor the return to sinus rhythm in the animal. FIG. 12 depicts a comparison of the animal before and after administration of flecainide using the smartphone, which again showed a conversion back to sinus rhythm in the animal.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a subject suffering from cardiac arrhythmia, comprising:
    (a) monitoring an incidence of said cardiac arrhythmia in said subject with aid of an electronic monitoring device;
    (b) administering an aerosolized pharmaceutical composition from an aerosolization device to said subject, wherein said aerosolized pharmaceutical composition comprises a therapeutically effective amount of at least one antiarrhythmic or a pharmaceutically acceptable salt thereof; and
    (c) receiving a treatment recommendation from said electronic monitoring device after said electronic monitoring device verifies said administering of said aerosolized pharmaceutical composition.

2. The method of claim 1, wherein said aerosolization device comprises an inhaler.

3. The method of claim 2, wherein said inhaler is in communication with said electronic monitoring device.

4. The method of claim 2, wherein said inhaler comprises a digital display.

5. The method of claim 2, wherein said inhaler comprises auditory means capable of communicating to said subject.

6. The method of claim 1, wherein said administering is performed by said subject.

7. The method of claim 1, wherein said administering is performed by a healthcare professional.

8. The method of claim 1, wherein said at least one antiarrhythmic or pharmaceutically acceptable salt thereof is a class I antiarrhythmic, class II antiarrhythmic, class III antiarrhythmic, class IV antiarrhythmic, class V antiarrhythmic, or a salt of any of these.

9. The method of claim 1, wherein said at least one antiarrhythmic or pharmaceutically acceptable salt thereof comprises flecainide acetate.

10. The method of claim 1, wherein said electronic monitoring device waits for a confirmation from a healthcare provider prior to allowing said administering of said aerosolized pharmaceutical composition to said subject.

11. The method of claim 1, wherein said therapeutically effective amount is an amount sufficient to convert said arrhythmia to normal sinus rhythm.

12. The method of claim 1, wherein said therapeutically effective amount is at least about 30 mg of said at least one antiarrhythmic or a pharmaceutically acceptable salt thereof.

13. The method of claim 1, wherein said therapeutically effective amount converts said arrhythmia to normal sinus rhythm from about 0 secs to about 2 hours after said administration.

14. The method of claim 1, wherein said electronic monitoring device is in communication with an electronic monitoring chip that is inserted into said subject or worn by said subject.

15. The method of claim 1, wherein said electronic monitoring device comprises a digital display or auditory means capable of communicating to said subject.

16. The method of claim 1, wherein said electronic monitoring device is a smartphone.

17. The method of claim 1, wherein said treatment recommendation comprises stopping said administering when said cardiac arrhythmia is converted to a normal sinus rhythm.

18. The method of claim 1, wherein said treatment recommendation comprises seeking medical attention when said cardiac arrhythmia does not respond to said administering.

* * * * *